(12) United States Patent
Dutta

(10) Patent No.: US 11,596,805 B2
(45) Date of Patent: Mar. 7, 2023

(54) LUMINAIRE FOR ENHANCED COLOR RENDITION AND WELLNESS

(71) Applicant: LEDVANCE LLC, Wilmington, MA (US)

(72) Inventor: Arunava Dutta, Winchester, MA (US)

(73) Assignee: LEDVANCE LLC, Wilmington, MA (US)

(*) Notice: Subject to any disclaimer, the term of this patent is extended or adjusted under 35 U.S.C. 154(b) by 0 days.

(21) Appl. No.: 17/946,296

(22) Filed: Sep. 16, 2022

(65) Prior Publication Data

US 2023/0019932 A1     Jan. 19, 2023

Related U.S. Application Data

(63) Continuation of application No. 17/519,194, filed on Nov. 4, 2021, now Pat. No. 11,478,659, which is a continuation of application No. 16/213,607, filed on Dec. 7, 2018, now Pat. No. 11,202,920.

(51) Int. Cl.
| | |
|---|---|
| *A61N 5/06* | (2006.01) |
| *F21V 19/00* | (2006.01) |
| *F21Y 103/10* | (2016.01) |
| *F21Y 115/10* | (2016.01) |

(52) U.S. Cl.
CPC .......... *A61N 5/0618* (2013.01); *F21V 19/001* (2013.01); *A61N 2005/0651* (2013.01); *A61N 2005/0663* (2013.01); *F21Y 2103/10* (2016.08); *F21Y 2115/10* (2016.08); *H05K 2201/10106* (2013.01)

(58) Field of Classification Search
CPC .......... F21S 10/02–026; F21V 9/30–45; F21V 19/001; A61N 5/0618; A61N 2005/0663; A61N 2005/0651; H05K 2201/10106; F21Y 2103/10; F21Y 2115/10; F21K 9/27
See application file for complete search history.

(56) References Cited

U.S. PATENT DOCUMENTS

| | | | | |
|---|---|---|---|---|
| 10,196,565 | B2* | 2/2019 | Vick | F21K 9/64 |
| 10,701,775 | B2* | 6/2020 | Petluri | A61N 5/0618 |
| 10,750,591 | B2* | 8/2020 | Petluri | H05B 45/20 |
| 11,202,920 | B2* | 12/2021 | Dutta | A61N 5/0618 |
| 11,478,659 | B2* | 10/2022 | Dutta | F21V 19/001 |
| 2018/0160490 | A1* | 6/2018 | Li | H05B 47/16 |
| 2020/0113022 | A1* | 4/2020 | Cahalane | F21V 5/007 |

* cited by examiner

*Primary Examiner* — Tracie Y Green
(74) *Attorney, Agent, or Firm* — Tutunjian & Bitetto PC

(57) ABSTRACT

In one aspect, a luminaire is provided for illumination, in which the luminaire has a normalized spectral power distribution (SPD) curve for promoting human wellness, the normalized SPD curve having the following percentage areas for the following wavelength domains, the normalized SPD curve including spectral energy in a 620 nm to 640 nm region of the SPD curve ranging from 9.5% to 10.5% of a total of an area for a normalized SPD curve; spectral energy in a 640 nm to 660 nm region of the SPD curve ranging from 7.25% to 9.8% of the total of the area of the normalized SPD curve; spectral energy in a 660 nm to 680 nm region of the SPD curve ranging from 4.8% to 7.8% of the total of the area for the normalized SPD curve; spectral energy in a 680 nm to 700 nm region of the SPD curve ranging from 2.75% to 5.5% of the total of the area for the normalized SPD curve; and a remainder of spectral energy of the total normalized SPD curve is in a 400 nm to 620 nm region area of the SPD curve.

20 Claims, 12 Drawing Sheets

TABLE I : Sphere Photometry of Comparative Sample Luminaire

|  | Lum Std 2 | Lum Std 1 |
|---|---|---|
| x | 0.3834 | 0.3769 |
| y | 0.3804 | 0.3731 |
| CCT | 3947 | 4072 |
| Duv | 0.0008 | -0.0007 |
| CRI | 84 | 83 |
| R9 | 16 | 13 |
|  |  |  |
| R1 | 82 | 82 |
| R2 | 90 | 87 |
| R3 | 95 | 92 |
| R4 | 81 | 84 |
| R5 | 82 | 83 |
| R6 | 86 | 84 |
| R7 | 87 | 86 |
| R8 | 67 | 68 |
| R9 | 16 | 13 |
| R10 | 76 | 71 |
| R11 | 80 | 84 |
| R12 | 59 | 71 |
| R13 | 84 | 83 |
| R14 | 97 | 95 |
| R15 | 77 | 76 |
|  |  |  |
| Rf | 82 | 82 |
| Rg | 95 | 98 |

FIG. 5

TABLE II : Sphere Photometry of Test Sample Luminaire

| | QOL A3D LUM | QOL A5D LUM |
|---|---|---|
| x | 0.3791 | 0.3854 |
| y | 0.3728 | 0.3708 |
| CCT | 4008 | 3819 |
| Duv | -0.0015 | -0.0042 |
| CRI | 94 | 96 |
| R1 | 96 | 97 |
| R2 | 96 | 99 |
| R3 | 96 | 93 |
| R4 | 96 | 94 |
| R5 | 95 | 98 |
| R6 | 94 | 96 |
| R7 | 94 | 96 |
| R8 | 85 | 95 |
| R9 | 61 | 92 |
| R10 | 91 | 96 |
| R11 | 94 | 93 |
| R12 | 75 | 86 |
| R13 | 96 | 98 |
| R14 | 97 | 96 |
| R15 | 92 | 96 |
| Rf | 90 | 94 |
| Rg | 101 | 104 |

FIG. 8

TABLE III: Comparison of enhanced luminaire vs. standard luminaire

| | w/ optics | -opt | +opt | no optics |
|---|---|---|---|---|
| x | 0.3791 | 0.3834 | 0.3769 | 0.3854 |
| y | 0.3728 | 0.3804 | 0.3731 | 0.3708 |
| CCT | 4008 | 3947 | 4072 | 3819 |
| Duv | 0.0015 | 0.0008 | 0.0007 | 0.0042 |
| CRI | 94 | 84 | 83 | 96 |
| R9 | 61 | 16 | 13 | 92 |
| | | | | |
| R1 | 96 | 82 | 82 | 97 |
| R2 | 96 | 90 | 87 | 99 |
| R3 | 96 | 95 | 93 | 93 |
| R4 | 96 | 81 | 84 | 94 |
| R5 | 95 | 82 | 83 | 98 |
| R6 | 94 | 86 | 84 | 96 |
| R7 | 94 | 87 | 86 | 96 |
| R8 | 85 | 67 | 68 | 95 |
| R9 | 61 | 16 | 13 | 92 |
| R10 | 91 | 76 | 71 | 96 |
| R11 | 94 | 80 | 84 | 93 |
| R12 | 75 | 59 | 71 | 86 |
| R13 | 96 | 84 | 83 | 98 |
| R14 | 97 | 97 | 95 | 96 |
| R15 | 92 | 77 | 76 | 96 |
| | | | | |
| Ra | 90 | 82 | 82 | 94 |
| Rf | 101 | 95 | 98 | 104 |

FIG. 10

TABLE IV: Area under the luminaire SPD curves

| nm | Std LED 1 % Area | Std LED 2 % Area | QOL A3D LUM % Area | QOL A5D LUM % Area |
|---|---|---|---|---|
| 400-420 | 0.95 | 0.36 | 0.36 | 0.51 |
| 420-440 | 5.83 | 1.69 | 1.98 | 2.69 |
| 440-460 | 8.45 | 9.34 | 10.08 | 8.03 |
| 460-480 | 3.77 | 6.03 | 4.58 | 4.15 |
| 480-500 | 4.27 | 3.9 | 4.34 | 4.65 |
| 500-520 | 6.90 | 6.41 | 7.59 | 6.47 |
| 520-540 | 8.30 | 8.32 | 8.52 | 7.24 |
| 540-560 | 9.23 | 9.38 | 8.24 | 7.85 |
| 560-580 | 10.29 | 10.54 | 8.68 | 7.94 |
| 580-600 | 11.08 | 11.35 | 10 | 8.18 |
| 600-620 | 10.56 | 10.89 | 10.73 | 9.28 |
| 620-640 | 8.56 | 8.95 | 9.68 | 10.23 |
| 640-660 | 5.97 | 6.38 | 7.36 | 9.69 |
| 660-680 | 3.71 | 4.07 | 4.9 | 7.73 |
| 680-700 | 2.15 | 2.39 | 2.98 | 5.35 |

FIG. 12

LUMINAIRE FOR ENHANCED COLOR RENDITION AND WELLNESS

CROSS REFERENCE TO RELATED APPLICATION

This patent application is a Continuation and claims benefit and priority to U.S. patent application Ser. No. 17/519,194, titled "LUMINAIRE FOR ENHANCED COLOR RENDITION AND WELLNESS" filed on Nov. 4, 2021, which claims priority to U.S. Pat. No. 11,202,920 granted on Dec. 12, 2021, which are herein incorporated by reference in their entirety.

TECHNICAL FIELD

The present disclosure generally relates to luminaires employing light emitting diodes, and more particularly to achieving spectrums of light using LEDs for providing enhanced color rendition and wellness of human beings.

BACKGROUND

As humans focus more on general wellness, how we feel in our surroundings is becoming increasingly important. By surroundings we mean environments where we spend a considerable portion of our daily lives. These would include one or more of the following depending on the age group, health, socio-economic status and role of the person: home, office, medical establishment, retirement community, manufacturing facility, school, grocery store, department store, automotive showroom etc.

In each of these environments, people handle or interface with different objects. These objects can have pastel colors, saturated colors or a combination thereof. If the color of these objects looks unattractive, people are less prone to handle them unless they have no other choice. This will affect how people feel in that environment: calm, comfortable and relaxed or uncomfortable, tense and irritated. The lighting that is used for the environment will have a profound effect on this.

It is important, therefore, to design luminaires/fixtures that produce a spectrum with a high quality of light that renders surrounding colored objects very well resulting in a calm, comfortable and relaxed environment that in turn promotes human wellness. These objects, as has been mentioned earlier, can have pastel colors, saturated colors or a combination thereof.

Another parameter of significant importance in wellness is what people think of their skin tone in the environment that they find themselves in. If the skin color is rendered poorly in the environment, people feel unhappy and stressed. This in turn affects their attentiveness and behavior. Also, humans come in a wide variety of skin tones and Caucasian skin tones are quite different from Asian skin tones, for example. The lighting that is used for the environment will have a profound effect on this.

It is important, therefore, to design luminaires/fixtures that produce a spectrum with a high quality of light that renders skin tones well resulting in a calm, comfortable and relaxed environment that in turn promotes human wellness.

SUMMARY

In some embodiments, methods and structures are provided for producing a luminaire that has a spectral power distribution for promoting human wellness.

In one aspect, a luminaire is provided for illumination that has a normalized spectral power distribution (SPD) curve for promoting human wellness, the normalized SPD curve having the following percentage areas for the following wavelength domains, the normalized SPD curve comprising spectral energy in the 540 nm to 560 nm region of the SPD curve ranging from 7.85% to 8.25% of a total for the area of the SPD curve, the normalized SPD curve comprising spectral energy in the 560 nm to 580 nm region of the SPD curve ranging from 7.95% to 8.7% of a total for the area of the SPD curve, the normalized SPD curve comprising spectral energy in the 580 nm to 600 nm region of the SPD curve ranging from 8.15% to 10% of a total for the area of the SPD curve, the normalized SPD curve comprising spectral energy in the 600 nm to 620 nm region of the SPD curve ranging from 9.15% to 10.75% of a total for the area of the SPD curve; spectral energy in the 620 nm to 640 nm region of the SPD curve ranging from 9.5% to 10.5% of the total for the area of the SPD curve; spectral energy in the 640 nm to 660 nm region of the SPD curve ranging from 7.25% to 9.8% of the total for the area of the SPD curve; spectral energy in the 660 nm to 680 nm region of the SPD curve ranging from 4.8% to 7.8% of the total for the area of the SPD curve; spectral energy in the 680 nm to 700 nm region of the SPD curve ranging from 2.75% to 5.5% of the total for the area of the SPD curve; and a remainder of spectral energy for the normalized SPD curve in an area in the 400-540 nm region of the SPD curve. One SPD difference between the standard luminaires and the enhanced luminaires that emit light that promote wellness starts from wavelengths greater than about 540 nm. The enhanced luminaires that promote wellness emit less percentage spectral energy in the 540 nm to 620 nm region than the standard luminaires. The enhanced luminaires that promote human wellness emit more percentage spectral energy in the 620 nm to 700 nm region than standard luminaires.

In another aspect, a method of lighting is provided for promoting human wellness by increasing representation of saturated color indexes in lighting. In one embodiment, the method of lighting can begin with employing a luminaire that has a normalized spectral power distribution (SPD) curve for promoting human wellness, the normalized SPD curve having the following percentage areas for the following wavelength domains, the normalized SPD curve comprising spectral energy in the 540 nm to 560 nm region of the SPD curve ranging from 7.85% to 8.25% of a total for the area of the SPD curve, the normalized SPD curve comprising spectral energy in the 560 nm to 580 nm region of the SPD curve ranging from 7.95% to 8.7% of a total for the area of the SPD curve, the normalized SPD curve comprising spectral energy in the 580 nm to 600 nm region of the SPD curve ranging from 8.15% to 10% of a total for the area of the SPD curve, the normalized SPD curve comprising spectral energy in the 600 nm to 620 nm region of the SPD curve ranging from 9.15% to 10.75% of a total for the area of the SPD curve; spectral energy in the 620 nm to 640 nm region of the SPD curve ranging from 9.5% to 10.5% of the total for the area of the SPD curve; spectral energy in the 640 nm to 660 nm region of the SPD curve ranging from 7.25% to 9.8% of the total for the area of the SPD curve; spectral energy in the 660 nm to 680 nm region of the SPD curve ranging from 4.8% to 7.8% of the total for the area of the SPD curve; spectral energy in the 680 nm to 700 nm region of the SPD curve ranging from 2.75% to 5.5% of the total for the area of the SPD curve; and a remainder of spectral energy for the normalized SPD curve in an area in the 400-540 nm region of the SPD curve. One SPD difference between the standard luminaires and the enhanced luminaires that emit light that promote wellness starts from wavelengths greater than about 540 nm. The enhanced luminaires that promote wellness emit less percentage spectral energy in the 540 nm to 620 nm region than the standard luminaires. The enhanced luminaires that promote human wellness emit more percentage spectral energy in the 620 nm to 700 nm region than standard luminaires. The method can continue with illuminating an area with the luminaire to provide color indices for saturated light selected from the group consisting of R9, R10, R11, R12 and combinations thereof, the color indices for the saturated light having values greater than 60.

In another aspect, a method of lighting is provided for promoting human wellness by increasing representation of lighting indices for illuminating skin tones. In one embodiment, the method of lighting includes employing a luminaire with a normalized spectral power distribution (SPD) curve for promoting human wellness, the normalized SPD curve having the following percentage areas for the following wavelength domains, the normalized SPD curve comprising spectral energy in the 540 nm to 560 nm region of the SPD curve ranging from 7.85% to 8.25% of a total for the area of the SPD curve, the normalized SPD curve comprising spectral energy in the 560 nm to 580 nm region of the SPD curve ranging from 7.95% to 8.7% of a total for the area of the SPD curve, the normalized SPD curve comprising spectral energy in the 580 nm to 600 nm region of the SPD curve ranging from 8.15% to 10% of a total for the area of the SPD curve, the normalized SPD curve comprising spectral energy in the 600 nm to 620 nm region of the SPD curve ranging from 9.15% to 10.75% of a total for the area of the SPD curve; spectral energy in the 620 nm to 640 nm region of the SPD curve ranging from 9.5% to 10.5% of the total for the area of the SPD curve; spectral energy in the 640 nm to 660 nm region of the SPD curve ranging from 7.25% to 9.8% of the total for the area of the SPD curve; spectral energy in the 660 nm to 680 nm region of the SPD curve ranging from 4.8% to 7.8% of the total for the area of the SPD curve; spectral energy in the 680 nm to 700 nm region of the SPD curve ranging from 2.75% to 5.5% of the total for the area of the SPD curve; and a remainder of spectral energy for the normalized SPD curve in an area in the 400-540 nm region of the SPD curve. One SPD difference between the standard luminaires and the enhanced luminaires that emit light that promote wellness starts from wavelengths greater than about 540 nm. The enhanced luminaires that promote wellness emit less percentage spectral energy in the 540 nm to 620 nm region than the standard luminaires. The enhanced luminaires that promote human wellness emit more percentage spectral energy in the 620 nm to 700 nm region than standard luminaires. The method further includes illuminating an area with the luminaire to provide color indices for illuminating skin tones selected from the group consisting of R13 and R15 and combinations thereof, the color indices for illuminating skin tones having values greater 90.

These and other features and advantages will become apparent from the following detailed description of illustrative embodiments thereof, which is to be read in connection with the accompanying drawings.

BRIEF DESCRIPTION OF THE DRAWINGS

The following description will provide details of embodiments with reference to the following figures wherein:

FIG. 5 includes TABLE I, which is a recordation of the data collected by sphere photometry measurements from the light emitted by the comparative luminaire samples.

FIG. 8 includes TABLE II, which is a recordation of the data collected by sphere photometry measurements from the light emitted by the test luminaire samples, in accordance with some embodiments of the present disclosure.

FIG. 10 includes TABLE III that includes a list of the spectral properties of the comparative sample luminaires for comparison with the test sample luminaires.

FIG. 12 includes TABLE IV that includes a list of the % areas under the normalized SPD curves of the comparative sample luminaires for comparison with the test sample luminaires

DETAILED DESCRIPTION

Figure 1:
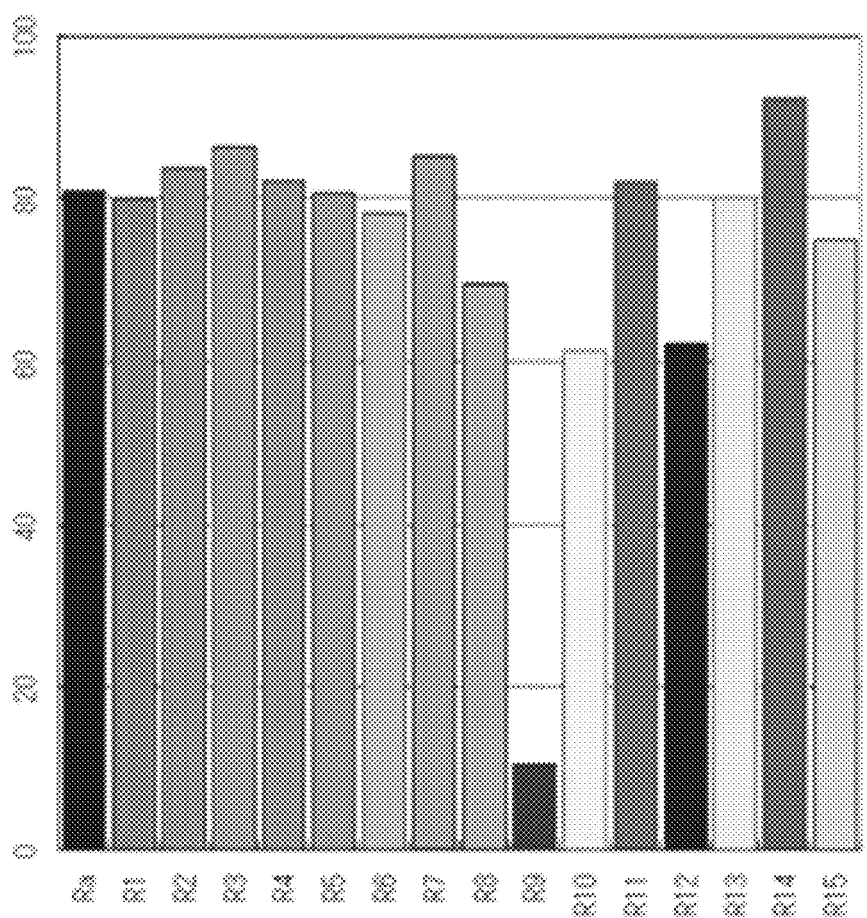
FIG. 1 is a plot, i.e., bar graph, illustrating typical color indices values, i.e., R1-R15, for a commercial standard luminaire.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

The methods and structures of the present disclosure illustrate how certain SPDs, spectral power distributions, of the luminaire can produce high values of the various color indices which in turn promotes human wellness. The spectral energy distribution of these SPD curves promote wellness. This results in a new understanding, unavailable before, of the percentage of the total spectral energy of the wellness promoting luminaire that is emitted over different wavelength regions of the entire visible spectrum. The methods and structures described herein describe spectral characteristics of luminaires that lead to higher values of the color indices R1 through R15 than standard luminaires. The methods and structures described herein focus attention not only on the pastel color indices R1 thru R8, which together determine the CRI, but also on the saturated color indices R9 thru R12 and the skin tone color indices R13 and R15. A color rendering index (CRI) is a quantitative measure of the ability of a luminaire to reveal the colors of various objects faithfully in comparison with an ideal or natural light source. The methods and structures of the present disclosure are also described with the TM30-15 color metrics like the fidelity metric Rf and the gamut metric Rg.

In the course of their daily lives, people spend time in a variety of environments, in which humans handle or interface with different objects and other human beings. If the colors of these objects look unattractive, people are less prone to handle them unless they have no other choice. This will affect how people feel in that environment: calm, comfortable and relaxed or uncomfortable, tense and irritated. The lighting that is used for the environment will have a profound effect on this since it affects how the objects look.

In terms of spectral properties of lighting, previously designed commercial luminaires do not consider wellness and its link to the spectral power distribution (SPD). Individual indices of CRI (i.e. R1 thru R8) are not quantified though. Prior luminaires do not consider the specifics of each of the saturated color indices R9 thru R12; and/or consider the skin tone rendition via indices R13 and R15. Additionally, existing luminaires do not consider information on spectral energy content of the emitted light as a function of wavelength.

The methods and structures provided herein provide luminaires/fixtures that produce a spectrum with a high quality of light that renders surrounding colored objects very well resulting in a calm, comfortable and relaxed environment that in turn promotes human wellness. These objects, as has been mentioned earlier, can have pastel colors, saturated colors or a combination thereof. More particularly, the methods and structures described herein focus attention not only on the pastel color indices R1 thru R8, which together determine the CRI, but very importantly also on the saturated color indices R9 thru R12.

In one aspect, a luminaire is provided for illumination, in which the luminaire has a normalized spectral power distribution (SPD) curve for promoting human wellness, the normalized SPD curve having the following percentage areas for the following wavelength domains, the normalized SPD curve comprising spectral energy in the 540 nm to 560 nm region of the SPD curve ranging from 7.85% to 8.25% of a total for the area of the SPD curve, the normalized SPD curve comprising spectral energy in the 560 nm to 580 nm region of the SPD curve ranging from 7.95% to 8.7% of a total for the area of the SPD curve, the normalized SPD curve comprising spectral energy in the 580 nm to 600 nm region of the SPD curve ranging from 8.15% to 10% of a total for the area of the SPD curve, the normalized SPD curve comprising spectral energy in the 600 nm to 620 nm region of the SPD curve ranging from 9.15% to 10.75% of a total for the area of the SPD curve; spectral energy in the 620 nm to 640 nm region of the SPD curve ranging from 9.5% to 10.5% of the total for the area of the SPD curve; spectral energy in the 640 nm to 660 nm region of the SPD curve ranging from 7.25% to 9.8% of the total for the area of the SPD curve; spectral energy in the 660 nm to 680 nm region of the SPD curve ranging from 4.8% to 7.8% of the total for the area of the SPD curve; spectral energy in the 680 nm to 700 nm region of the SPD curve ranging from 2.75% to 5.5% of the total for the area of the SPD curve; and a remainder of spectral energy for the normalized SPD curve in an area in the 400 nm to 540 nm region of the SPD curve.

In some embodiments, the SPD difference between the standard luminaires and the enhanced luminaires which emit light that promote wellness starts from wavelengths greater than about 540 nm. The enhanced luminaires that promote wellness emit less percentage spectral energy in the 540-620 nm region than the standard luminaires. The enhanced luminaires that promote human wellness emit more percentage spectral energy in the 620-700 nm region than standard luminaires.

Another lighting parameter of importance for wellness is what people think of their skin tone in a lighting environment. If the skin color is rendered poorly by the lighting, people feel unhappy and stressed in that environment. This in turn affects their attentiveness and behavior. Thus, wellness is sacrificed. Also, humans come in a wide variety of skin tones and Caucasian skin tones are quite different from Asian skin tones for example. The lighting that is used for the environment will have a profound effect on how the skin color is rendered. It is important, therefore, to design luminaires/fixtures that produce a spectrum with a high quality of light that renders skin tones well resulting in a calm, comfortable and relaxed environment that in turn promotes human wellness. For example, R13 is relevant for Caucasian skin tone, while R15 is relevant for Asian skin tone. A method of lighting is provided for promoting human wellness by increasing representation of lighting indices for illuminating skin tones.

In one embodiment, the method of lighting includes employing a luminaire with a normalized spectral power distribution (SPD) curve for promoting human wellness, the normalized SPD curve having the following percentage areas for the following wavelength domains, the normalized SPD curve comprising spectral energy in the 540 nm to 560 nm region of the SPD curve ranging from 7.85% to 8.25% of a total for the area of the SPD curve, the normalized SPD curve comprising spectral energy in the 560 nm to 580 nm region of the SPD curve ranging from 7.95% to 8.7% of a total for the area of the SPD curve, the normalized SPD curve comprising spectral energy in the 580 nm to 600 nm region of the SPD curve ranging from 8.15% to 10% of a total for the area of the SPD curve, the normalized SPD curve comprising spectral energy in the 600 nm to 620 nm region of the SPD curve ranging from 9.15% to 10.75% of a total for the area of the SPD curve; spectral energy in the 620 nm to 640 nm region of the SPD curve ranging from 9.5% to 10.5% of the total for the area of the SPD curve; the spectral energy in the 640 nm to 660 nm region of the SPD curve ranging from 7.25% to 9.8% of the total for the area of the SPD curve; spectral energy in the 660 nm to 680 nm region of the SPD curve ranging from 4.8% to 7.8% of the total for the area of the SPD curve; spectral energy in the 680 nm to 700 nm region of the SPD curve ranging from 2.75% to 5.5% of the total for the area of the SPD curve; and a remainder of spectral energy for the normalized SPD curve in an area in the 400 nm to 540 nm region of the SPD curve. The SPD difference between the standard luminaires and the enhanced luminaires which emit light that promote wellness starts from wavelengths greater than about 540 nm. The enhanced luminaires that promote wellness emit less percentage spectral energy in the 540-620 nm region than the standard luminaires. The enhanced luminaires that promote human wellness emit more percentage spectral energy in the 620 nm to 700 nm region than standard luminaires. The method further includes illuminating an area with the luminaire to provide color indices for illuminating skin tones selected from the group consisting of R13 and R15 and combinations thereof, the color indices for illuminating skin tones having values greater 90. The methods and structures of the present disclosure are now described in greater detail with reference to FIGS. 1 to 11.

FIG. 1 is a plot, i.e., bar graph illustrating typical values of color indices, i.e., R1-R15, for a commercial standard luminaire. For approximately the past 50 years, the metric employed to characterize light emitted from a luminaire type light source has been the color rendition index (CRI). The color rendering index (CRI) is a quantitative measure of the ability of a luminaire to reveal the colors of various objects faithfully in comparison with an ideal or natural light source. The color rendering index (CRI) is defined by the International Commission on Illumination (CIE) as follows: Color rendering: Effect of an illuminant on the color appearance of objects by conscious or subconscious comparison with their color appearance under a reference illuminant. The reference illuminants proposed by the CIE for the calculation of the color rendering index (CRI) may be a blackbody radiator or a daylight phase of the same correlated color temperature (CCT) as the test source for CCTs respectively below or above 5000° K. CRI compares the color rendition of eight pastel (unsaturated) colors illuminated by the luminaire under the test vs. standard light source, e.g., black body, at the same color temperature. The pastel colors indices are designated R1 through R8. CRI is an approximate quantification of the ability of the luminaire to render colored objects and is the average of the color indices R1 through R8.

FIG. 1 shows the typical color indices R1 through R15 for a conventional light emitting diode (LED) luminaire. FIG. 1 is provided to generally illustrate the levels of color indices for luminaires that are in the market, but it is not intended that the combination of color indices depicted in FIG. 1 be directed to any specific luminaire. The maximum value of any of the color indices, e.g., from R1 through R15, is 100. As illustrated in FIG. 1, the pastel color indices R1 through R8 are emitted at a value greater than 80 with the exception of R6 which is in the high 70s.

The CRI metric has several deficiencies. While it has been a decent metric for traditional lighting, e.g., incandescent lighting, it has several deficiencies when it comes to solid state lighting, such as a light emitting diode (LED). The term "solid state" refers to light emitted by solid-state electroluminescence, as opposed to incandescent bulbs (which use thermal radiation) or fluorescent tubes, which use a low-pressure Hg discharge. In a broad sense, a light emitting diode (LED) is a semiconductor device that emits visible light when an electric current passes through it. Some examples of solid state light emitters that are suitable for the methods and structures described herein include inorganic semiconductor light-emitting diodes (LEDs), organic light-emitting diodes (OLED), polymer light-emitting diodes (PLED) or combinations thereof.

Saturated colors are not included in the CRI calculation. Color indices R9 through R12 cover saturated colors. For example, for saturated colors: R9 is red, R10 is yellow, R11 is green and R12 is blue. The saturated colors indices R9 through R12 in the emitted light from LED luminaires are often quite low leading to poor rendering of many objects. For example, standard LED luminaires may have index R9 from 5-20 which renders red colored objects very poorly. Red is a very common color in the environment. Yellows and blues R10 and R12 are also rendered poorly by standard LED luminaires along with green R11. The poor renditions of the aforementioned colors results in a poor perception of the environment, which in turn hurts the wellness sensation of the person.

Additionally, the CRI metric does not consider the human skin tone. Color index R13 and R15 address skin tones. R13 is relevant for Caucasian skin tone; and R15 is relevant for Asian skin tone. Of course, there is no single Caucasian skin tone, and even more so there is no single Asian skin tone, as variations can and do occur in each category. If a person feels that their skin color is being rendered poorly in a lighting environment, that person may react by being unhappy, annoyed and/or uncomfortable. This in turn hurts the wellness sensation of the person.

In commercial environments, such as retail establishments, e.g., clothing stores, office spaces, medical establishments, retirement communities, manufacturing facilities, schools and institutions of higher learning, grocery stores, department stores and automotive showrooms etc., vividness of whites and colors is extremely important for catching the attention of the customer and making him/her feel good with the purchase. Color rendering is also of great relevance in grocery stores where the shopper is attracted more towards fruits and vegetables and meats that look fresh and inviting. Here again it is a feeling of wellness that is sought for the consumer. One does not want to make a purchase and keep second guessing about the quality of the purchase. This would not make the person happy and would take away from the sense of wellness.

Color rendering is of further consequence in museums and art galleries where important art work is being displayed and saturated colors are abundantly used. It is also of significant relevance in hospitals where surgery is being performed or medical diagnosis is being made. Furthermore, as the population of the country ages, color rendition in assisted living and retirement communities will become increasingly important to deliver a good skin tone rendition which will keep the senior residents relaxed and happy resulting in a sense of wellness.

The illuminating engineering society (IES) has proposed another methodology called TM30-15 to measure the color rendition of a light source such as a LED luminaire. Unlike CRI which is a single metric, TM30-15 is a dual metric method. The main components of TM30 are the Fidelity Index (Rf) and the Gamut Index (Rg) and the Color Vector Graphic (CVG). Numerous sub-indices also exist.

The TM30-15 Rf calculation is based on a theoretical comparison of how 99 color samples (note that CRI uses 8 color samples, and these are all pastel colored) are rendered by the test luminaire and the reference illuminant, which is a blackbody (Planckian) radiator, a model of daylight, or a blend of the two. Gamut is the area enclosed by the chromaticity of a set of color samples. The Gamut Index Rg is an average measure of the saturation. Rg values >100 indicates an average increase in gamut, whereas Rg levels <100 indicate an average decrease in gamut.

In view of the above noted deficiencies in lighting, the methods and structures provide herein a luminaire 50 that provides both the light indices for pastels, i.e., indices R1-R8; and high concentrations for the light indices for saturated light, e.g., R9-R12. In some embodiments, the luminaire provided herein also provides a light index for Caucasian skin color, i.e., light indices R13, and light indices for Asian skin color, i.e., light indices R15.

In one aspect, a luminaire is provided for illumination, in which the luminaire has a normalized spectral power distribution (SPD) curve for promoting human wellness, the normalized SPD curve having the following percentage areas for the following wavelength domains, the normalized SPD curve comprising spectral energy in the 540 nm to 560 nm region of the SPD curve ranging from 7.85% to 8.25% of a total for the area of the SPD curve, the normalized SPD curve comprising spectral energy in the 560 nm to 580 nm region of the SPD curve ranging from 7.95% to 8.7% of a total for the area of the SPD curve, the normalized SPD curve comprising spectral energy in the 580 nm to 600 nm region of the SPD curve ranging from 8.15% to 10% of a total for the area of the SPD curve, the normalized SPD curve comprising spectral energy in the 600 nm to 620 nm region of the SPD curve ranging from 9.15% to 10.75% of a total for the area of the SPD curve; spectral energy in the 620 nm to 640 nm region of the SPD curve ranging from 9.5% to 10.5% of the total for the area of the SPD curve; spectral energy in the 640 nm to 660 nm region of the SPD curve ranging from 7.25% to 9.8% of the total for the area of the SPD curve; spectral energy in the 660 nm to 680 nm region of the SPD curve ranging from 4.8% to 7.8% of the total for the area of the SPD curve; spectral energy in the 680 nm to 700 nm region of the SPD curve ranging from 2.75% to 5.5% of the total for the area of the SPD curve; and a remainder of spectral energy for the normalized SPD curve in an area in the 400 nm to 540 nm region of the SPD curve.

Figure 11:
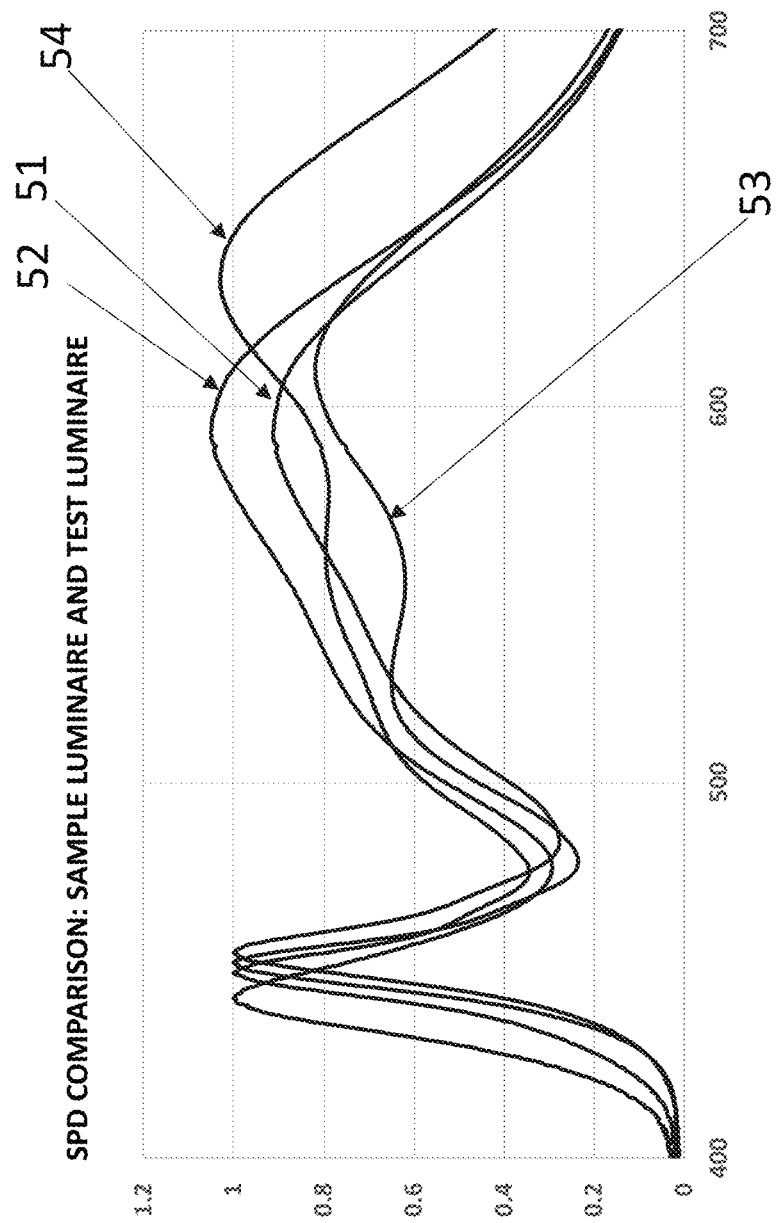
FIG. 11 is an overlay of the normalized spectral power distributions of standard luminaires, i.e., comparative sample luminaires, and the enhanced luminaires, i.e, test sample luminaires.

Examples of the spectral power distribution (SPD) curve for promoting human wellness are provided in FIG. 11, in which the plots of example spectral power distribution (SPD) curves providing the above values are identified by reference numbers 53 and 54.

In one embodiment, the remainder of the spectral energy includes spectral energy in the 400 nm to 420 nm region of the SPD curve ranging from 0.35% to 0.5% of the total for the area of the normalized SPD curve; spectral energy in the 420 nm to 440 nm region of the SPD curve ranging from 1.95% to 2.7% of the total for the area of the normalized SPD curve; spectral energy in the 440 nm to 460 nm region of the SPD curve ranging from 8% to 10.1% of the total for the area of the normalized SPD curve; spectral energy in the 460 nm to 480 nm region of the SPD curve ranging from 4% to 4.75% of the total for the area of the normalized SPD curve; spectral energy in the 480 nm to 500 nm region of the SPD curve ranging from 4.25% to 4.75% of the total for the area of the normalized SPD curve; spectral energy in the 500 nm to 520 nm region of the SPD curve ranging from 6.25% to 7.75% of the total for the area of the normalized SPD curve; and spectral energy in the 520 nm to 540 nm region of the SPD curve ranging from 7% to 9% of the total for the area of the normalized SPD curve.

The light emitted from the luminaire having the aforementioned spectral power distribution (SPD) curve has pastel color indices that comprise R1 being equal to or greater than 96, R2 being equal to or greater than 96; R3 being equal to or greater than 92; R4 being equal to or greater than 94; R5 being equal to or greater than 95; R6 being equal to or greater than 94; R7 being equal to or greater than 94; and R8 being equal to or greater than 85. The luminaire having the above characteristics has a color rending index (CRI) that is equal to 94 or greater.

The light emitted from the luminaire having the aforementioned spectral power distribution (SPD) curve can have saturated color indices selected from the group consisting of R9 ranging from 60 to 95, R10 ranging from 91 to 96, R11 ranging from 90 to 95, R12 ranging from 75 to 86, and combinations thereof.

The light emitted from the luminaire having the aforementioned spectral power distribution (SPD) curve can have skin tone indices selected from the group consisting of R13 being equal to 95 or greater, R15 being equal to 92 or greater, and combinations thereof. The light emitted from the light source comprises a correlated color temperature (CCT) ranging between 3500K and 5000K, and lumens per watt (LPW) value ranging from 95 to 125.

Figure 2A:
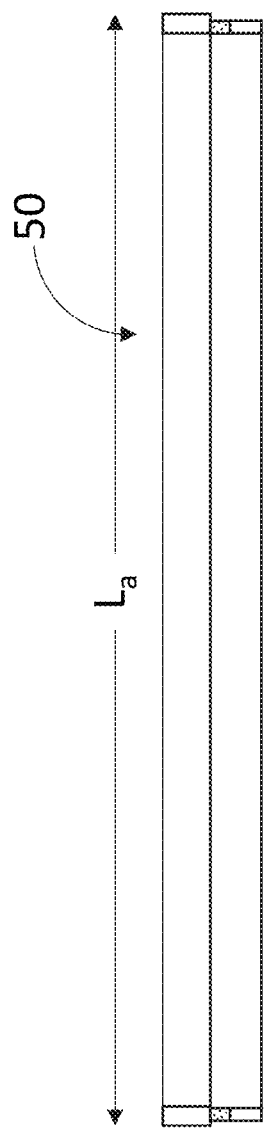
FIG. 2A is a side perspective view of a first embodiment of a linear luminaire including a solid state light source for enhanced color rendition and wellness in accordance with the present disclosure.
Figure 2B:
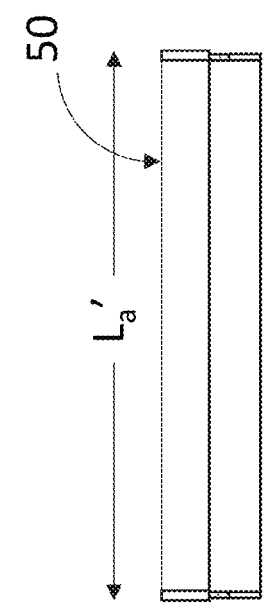
FIG. 2B is a side perspective view of a second embodiment of a linear luminaire including a solid state light source for enhanced color rendition and wellness, in accordance with the present disclosure.
Figure 2C:
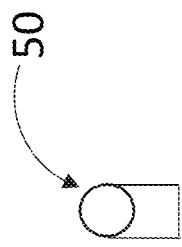
FIG. 2C is an end perspective view of the luminaire depicted in FIG. 2A and FIG. 2B.
Figure 3:
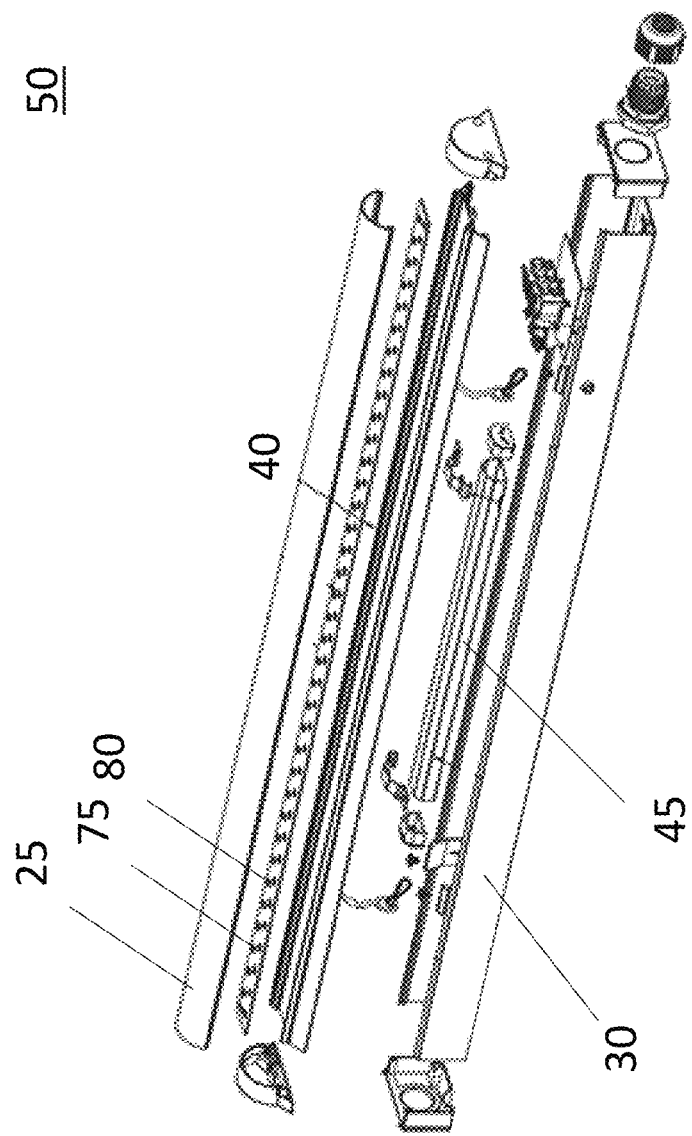
FIG. 3 is an exploded view of a luminaire including an LED light source that emits indices of light R1 thru R8 for pastels; at least one of the saturated color indices R9 thru R12; and/or emits skin tone rendition indices R13 and/or R15, in accordance with one embodiment of the present disclosure.

The structures depicted in FIGS. 2A-3 are employed for describing both test samples, and comparative samples, as discussed herein. In test samples, the LED type is selected to provide light indices for pastels, i.e., indices R1-R8; high values for the light indices for saturated light, e.g., R9-R12; a light index for Caucasian skin color, i.e., R13, and a light index for Asian skin color, i.e., R15. The test samples are referred to QOL A3D LUM and QOL A5D LUM, which are also referred to as enhanced luminaires. The test sample luminaires emit light having enhanced color rendition and wellness. Comparative samples are luminaires that provide light indices for pastels R1-R8; yet in comparison to the test samples are deficient in the light indices for saturated light, e.g., R9-R12; are deficient in light indices for Caucasian skin color, i.e., R13, and are deficient to light indices for Asian skin color, i.e., R15. The comparative samples may be referred to as LUM STD 1 and LUM STD2, which can also be referred to as standard luminaires.

The luminaire 50 includes a solid state light source, e.g., light emitting diode. The form factor for the luminaire 50 of the present disclosure may have a linear lamp form factor, e.g., linear lamp 50, as depicted in FIGS. 2A-3. FIG. 2A illustrates one embodiment of a luminaire 50 having a linear form factor, i.e., linear lamp 50, in which the length La of the linear lamp 50 is on the order of 4 feet. FIG. 2B illustrates one embodiment of a linear lamp 50 for a luminaire having a length La' of on the order of 2 feet. FIG. 2C illustrates an end of the luminaire 50 having an end cap. In some embodiments, the light source is integrated into a luminaire having a form factor of a linear fixture with an aspect ratio of 8 or greater.

FIG. 3 is an exploded view of a luminaire including an LED light source that emits indices of light R1 thru R8 for pastels; each of the saturated color indices R9 thru R12; and/or consider the skin tone rendition via indices R13 and R15. It is noted that the above examples for the length of the luminaire 50 are provided for illustrative purposes only. For example, in some instances, the aspect ratio of the linear fixture may range from 8 to 24. The structures depicted in FIGS. 2A-3 illustrate both comparative and test luminaires, in which the only difference between the luminaires is the light source for providing the different spectra.

Figure 4:
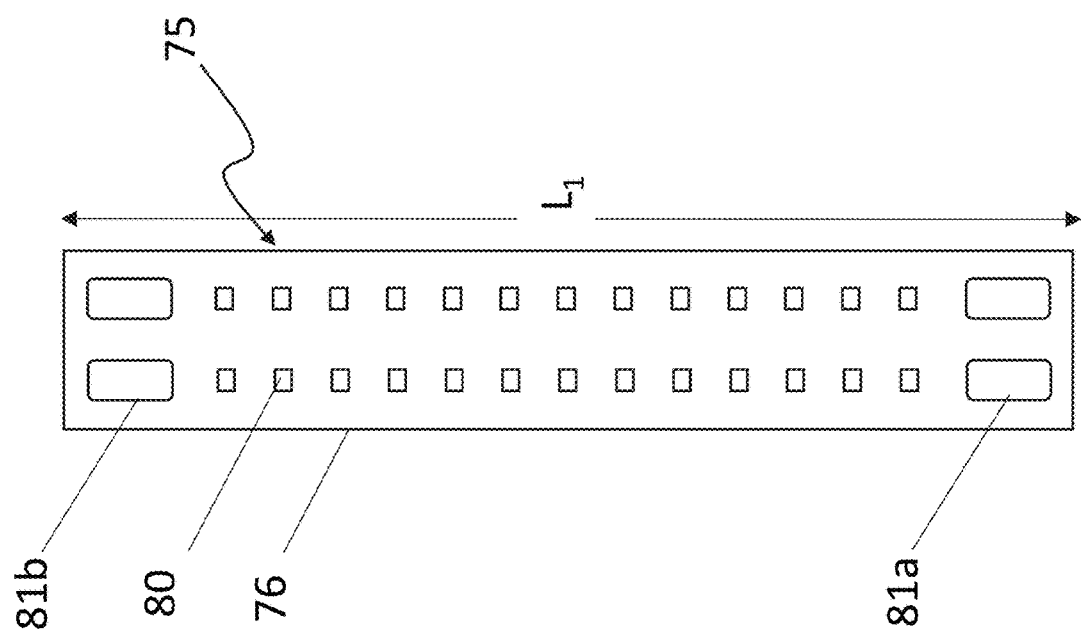
FIG. 4 is a perspective top down view of the light source which may consist of two or more rows of LEDs mounted to a linear substrate.

Referring to FIG. 4, in some embodiments, the light source 75 for the luminaire may consist of two rows of LEDs 80 mounted to a linear substrate 76. The linear substrate 76 may be a metal core printed circuit board (MCPCB). A metal core printed circuit board (MCPCB) is a board that incorporates a base metal material as a heat spreader as an integral part of the printed circuit board (PCB). Furthermore, MCPCB can take advantage of incorporating a dielectric polymer layer with high thermal conductivity for lower thermal resistance. A printed circuit board (PCB) mechanically supports and electrically connects electronic components, such as the LEDs 80 and the driving electronics, using conductive tracks, pads and other features etched from copper sheets laminated onto a non-conductive substrate. The printed circuit board can include a dielectric material. For example, the circuit board may be composed of fiber-reinforced plastic (FRP) (also called fiber-reinforced polymer, or fiber-reinforced plastic) is a composite material made of a polymer matrix reinforced with fibers. The fibers are usually glass, carbon, aramid, or basalt. The polymer is usually an epoxy, vinylester, or polyester thermosetting plastic, though phenol formaldehyde resins are still in use. In some embodiments, the printed circuit board (PCB) is composed of a composite consistent with the above description that is called FR-4. The printed circuit board may be made in one piece or in longitudinal sections joined by electrical bridge connectors.

In one example, the linear substrate 76 is a MCPCB substrate that is about 1 inch wide and is mounted on an aluminum (Al) heat sink, and the thermal interface is achieved by screws that affix the light engine board to the heat sink. The linear substrate 76 may include two rows of LEDs on the MCPCB with the DC power input leads 81a at one end of the light source 75; and similar power output leads 81b at the opposite end of the light source 75.

In some embodiments, the rows of LEDs 80 are mounted near the two edges of the light engine, i.e., light source 75. The LEDs 80 diodes, e.g., surface mount device (SMD) light emitting diodes (LED), are present on a circuit board, e.g., printed circuit board. A light emitting diode (LED) 80 is a light source that can be a semiconductor device that emits visible light when an electric current pass through it. The LEDs 80 of the light source 75 can include a plurality of series-connected or parallel-connected LEDs 80, or an LED array. At least one LED array for the light source can include a plurality of LED arrays. In the embodiment that is depicted in FIG. 4, the LEDs 80 are arranged in two columns, but it is not intended that an array of LEDs 80 be limited to only this arrangement. For example, the LEDs 80 may also be arranged in a single column that extends along most of the length of the circuit board 76.

Any type of LED may be used in the LEDs 80 of the light source 76. For example, the LEDs 80 of the light source 75 can be semiconductor LEDs, organic light emitting diodes (OLEDs), semiconductor dies that produce light in response to current, light emitting polymers, electro-luminescent strips (EL) or the like. The LEDs 80 can be mounted to the circuit board 76 by solder, a snap-fit connection, or other engagement mechanisms. In some examples, the LEDs 80 are provided by a plurality of surface mount device (SMD) light emitting diodes (LED) arranged in a plurality of lines on the circuit board 76.

The LEDs 80 are selected to provide test samples, or comparative samples, as discussed herein. In test samples, the LED type is selected to provide light indices for pastels, i.e., indices R1-R8; high levels for the light indices for saturated light, e.g., R9-R12; at least one light index for Caucasian skin color, i.e., R13, and at least one light index for Asian skin color, i.e., R15. The test samples are referred to QOL A3D LUM and QOL A5D LUM. The test sample luminaires emit light having enhanced color rendition and wellness. Comparative samples are luminaires that provide light indices for pastels R1-R8; yet in comparison to the test samples are deficient in the light indices for saturated light, e.g., R9-R12; are deficient in light indices for Caucasian skin color, i.e., R13, and are deficient in light indices for Asian skin color, i.e., R15. The comparative samples may be referred to as LUM STD 1 and LUM STD 2.

In one embodiment, the LEDs 80 for the light source 75 for LUM STD 1 and LUM STD 2 are type 2835 which means 2.8 mm by 3.5 mm form factor. The nominal correlated color temperature (CCT) of the LEDs 80 for the light source 75 for LUM STD 1 and LUM STD 2 is 4000K. There are 168 LEDs 80 on the light engine arranged with 14 LEDs in series in one string with 12 strings in parallel. The LEDs 80 for the light source 75 for LUM STD 1 and LUM STD 2 are nominal 3V and the nominal DC through the light engine load is about 720 mA, which amounts to about 60 mA DC through each of the 12 LED strings.

The LEDs 80 for the test luminaire samples, i.e., enhanced luminaires, can be selected to provide the spectral power distribution (SPD) curve for promoting human wellness, as depicted in FIG. 11, in which the plots of the spectral power distribution (SPD) curves for the enhanced luminaires are identified by reference numbers 53 and 54. In some examples, the LEDs 80 employed in the light sources 75 can emit various color temperatures (CCT). Color temperatures over 5000 K are called "cool colors" (bluish white), while lower color temperatures (2700-3000 K) are called "warm colors" (yellowish white through red). The LEDs 80 of the luminaires provided by the present disclosure in some embodiments can range from 2000K to 7000K. The LEDs 80 for each light source 75 may each be the same or they may be varied.

Referring to FIG. 3, the light source 75 for both the test samples, i.e., QOL A3D LUM and QOL A5D LUM, and comparative samples, i.e., LUM STD 1 and LUM STD 2 can be driven by a ballast 45 that is positioned in the luminaire housing 30 and below the heat sink 40. In some embodiments, the ballast 45 is fed from a 120-277V mains power supply. In some embodiments, the nominal input W for the strip luminaire is 32 W. The ballast 45 has 4 kV surge suppression and delivers constant current to the light engine 75. The ballast 45 can be designed to meet UL 1310 and UL48 Class 1 with built-in over temperature protection. Power factor is >0.9 and total harmonic distortion (THD) is <20%. The driver is 0-10V dimmable. Sheet metal is used for the housing 30 with a powder coat paint finish. A polycarbonate acrylic lens 25 provides a diffuse low glare light emission from the luminaire. The luminaire 50 can be surface, or suspension mounted.

Characterization for Comparative Sample Luminaire: LUM STD 2 Including Single 4' MCPCB The comparative sample luminaire having the structure described above with reference to FIGS. 2A-3 and including a light source 75 of LEDs 80 of commercially available type 2835 (type 2835 refers to the form factor of the LED: 2.8 mm by 3.5 mm), which is referred to LUM STD 2, was measured by sphere photometry. The data collected through sphere photometry measurements was recorded in TABLE I: Sphere Photometry of Comparative Sample Luminaire, which is depicted in FIG. 5 (hereafter referred to as TABLE I). TABLE I lists the spectral parameters for both LUM STD 2 and LUM STD1. Please refer to the column marked LUM STD 2 for the comparative sample luminaire having the structure described with reference to FIGS. 2A-3. LUM STD 2 had a nominal 4000K CCT with a color point just slightly above the black body curve as evidenced by the small positive value for the distance to the blackbody locus (Duv).

The color rendering index (CRI) for LUM STD 2 was 84 which is the mean of the pastel color indices R1 through R8 that are also listed in TABLE I. The value of 84 is a number that is typical of commercially available luminaires and it renders pastel colors in the manner of commercially available luminaires, i.e., the light emitted being provided in majority with pastel color indices, i.e., R1 through R8, with a substantially lesser emission of the color indices for the saturated colors, which include R9 through R12, while also having substantially lesser emission for the color indices recognized for favorable, i.e., attractive lighting, of Caucasian skin tone, i.e., R13, and Asian skin tone, i.e., R15. Referring to TABLE I, for LUM STD 2 the saturated color indices R9, R10, R11 and R12 are 16, 76, 80 and 59 for red, yellow, green and blue, respectively. As previously noted, the maximum value for a color index is 100. Each of the measurements for all four key saturated colors, i.e., R9-R12, is particularly low given that 100 is the maximum score. For example, the maximum color index score for the entirety of the saturated color indices was 80, with a lowest on the order of substantially being 15, e.g., 16. From the data, the range of saturated color rendering indices may range from 15 to 80 for the comparative luminaire sample LUM STD 2.

Referring to TABLE I, skin tone rendition was also poor, i.e., low, for the comparative luminaire sample LUM STD 2 for both Caucasian skin tones and Asian skin tones. Again, relative to the maximum color index value of 100, the measured R13 index for illumination of Caucasian skin tone was 84, which is low; and the measured R15 index for illumination of Asian skin tone was an even lower 77.

The TM-30 fidelity and gamut metrics Rf and Rg are 82 and 95, respectively indicating low color fidelity and low color saturation.

Figure 6:
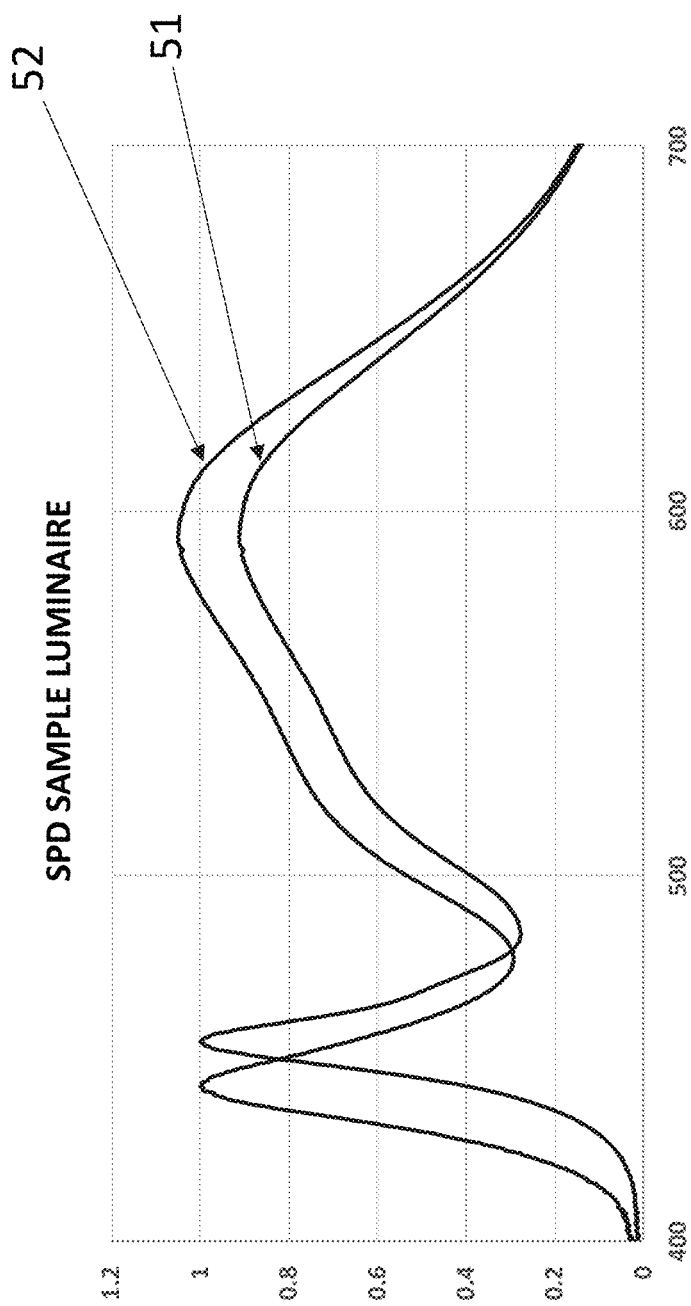
FIG. 6 depicts plots illustrating the spectral power distribution (SPD) of the light emitted by the comparative luminaire samples.

FIG. 6 shows the spectral power distribution (SPD) of the light emitted by the comparative luminaire sample LUM STD 2. The spectral power distribution (SPD) is graphically depicted in FIG. 6, in which the curve identified by reference number 51 illustrates the spectral power distribution (SPD) captured by the spectrometer attached to the sphere photometry system for the comparative luminaire sample LUM STD 2. The spectral power distribution (SPD) data is available as W/nm vs nm over the visible range of wavelengths 400-700 nm. The W/nm data was normalized by the peak intensity in the blue region resulting in a normalized intensity value of 1.0 for the peak in the blue. For the comparative luminaire sample LUM STD 2, this peak in the blue region occurs at a wavelength of 454.5 nm, as illustrated on the curve identified by reference number 51. It is observed from the normalized spectral power distribution (SPD) for comparative luminaire sample LUM STD 2 that there is a progressive increase in the normalized intensity value from around 490 nm resulting in another local maximum around 595 nm followed by a progressive decline throughout the red region, wherein the red region is >600 nm.

Interconnection of Multiple PCB Boards in Luminaire

The light engine 75 for comparative luminaire sample LUM STD 2 was a 4' long L1 MCPCB, as described with reference to FIGS. 2A-4. The 4' length of the MCPCB board makes the light emitting diode (LED) population of the board challenging due to the throw capabilities needed for the (LED) pick and place machine. An alternate design for the light engine 75 was created that employed six 8" long L2 MCPCB boards that are daisy chained by solder leads. This may be referred to as the interconnection of multiple PCB board in the luminaire.

The use of six shorter 8" long L2 MCPCB boards in place of the single 4' (48") long L1 MCPCB board of the same width used in the comparative luminaire sample LUM STD 2 essentially solves two limitations of the light engine 75 in comparative luminaire sample LUM STD 2, as described with reference to FIGS. 2A-4. For example, the interconnection, e.g., daisy chained connection, of the shorter, e.g., 8" long L2, MCPCB boards can provide for the use of standard pick and place equipment to transfer the LEDs to the shorter MCPCB boards rather than requiring very specialized pick and place equipment that has the throw to populate a 4' long L1 MCPCB board. Additionally, in comparison to a long MCPCB board, such as the 4' long MCPCB board that is employed in the light engine 75 for comparative luminaire sample LUM STD 2, as described with reference to FIGS. 2A-4, the shorter MCPCB boards, such as the 8" long MCPCB boards, can make use of a smaller reflow oven rather instead of requiring a large reflow oven to fix the LEDs 80 to the single 4' long light engine 75 board.

The use of the shorter L2 MCPCB boards that are interconnected to provide a large light engine 75 allows a design flexibility to create any custom SPD (spectral power distribution) from the luminaire with relative ease, an ability that is not possible with the single 48" long L1 board without considerable operational complexity.

Figure 7:
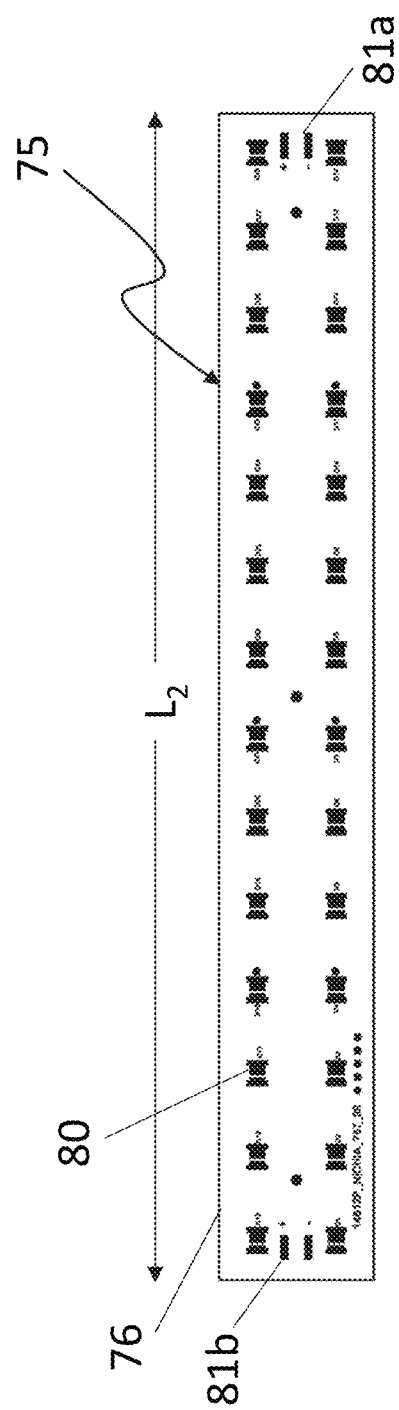
FIG. 7 is a perspective view depicting one example of an 8" long metal core printed circuit board that is about 1" wide, and provides the substrate for mounting the light emitting diodes (LEDs) of a light source, in accordance with one embodiment of the present disclosure.

FIG. 7 illustrates one example of 8" long L2 MCPCB boards which are about 1" wide. The PCB boards each include two strings of LEDs 80. More specifically, each board has 2 strings of LEDs 80 in parallel with 14 LEDs 80 in series in each string. In some embodiments, the MCPCB boards having the shorter length L2 depicted in FIG. 7 include LEDs 80, which are 3V type 2835 LEDs. In some embodiments, the MCPCB boards having the shorter length L2 depicted in FIG. 7 include LEDs 80, which are 3V type 2835 LEDs. In some embodiments, the MCPCB boards having the shorter length L2 depicted in FIG. 7 include LEDs 80, which are 3V Type 3030 LEDs. By "3030" as used to define an LED 80, it is meant that the form factor for the LED 80 is 3.0 mm×3.0 mm. For this discussion, it is implicit that the LEDs 80 are selected such that the 2835 LED emission spectrum is different from the 3030 LED emission spectrum.

In other words, the LED configuration for each of the 8" short boards is 14S2P. By daisy chaining six of these short boards we get a board with a LED configuration of 14S12P which is identical to the configuration of the LEDs in the 4' long light engine 75 of the original luminaire. It is possible to make the 4' long MCPCB by using any combination of the two 8" long MCPCB templates shown in FIG. 7. For example, one could conceive of the following 8" board combinations (boards are series connected by solder leads between boards) to realize the 4' long MCPCB: 6 type 2835 LED boards; 6 type 3030 boards; 4 type 2835 boards and 2 type 3030 boards; and 2 type 2835 boards and 4 type 3030 boards. It is noted that the aforementioned examples are provided for illustrative purposes only, and is not intended to limit the present disclosure. For example, the light sources 75 described herein, are not restricted to an even number of boards per LED type. In some embodiments, the light sources 75 may include an odd numbers of the boards too, e.g., 1 type 2835 board and 5 type 3030 boards.

Each one of these different board combinations will result in a different overall SPD from the luminaire since the selected 2835 LEDs have a different emission spectrum than the 3030 LEDs as has been mentioned above.

Characterization for Comparative Sample Luminaire: LUM STD 1 Including Multiple Interconnected MCPCB For comparative luminaire sample LUM STD 1, six short length L2 type MCPCB boards of the type shown in FIG. 7 were populated with another commercially available 2835 LED. These six MCPCBs were daisy chained, e.g., electrically interconnected by wire connection and solder joint, to form a light engine 75 dimensionally similar to the comparative luminaire sample LUM STD 2, e.g., being a 4' long light engine 75. The light engine 75 provided by the multiple interconnected MCPCBs is inserted as a substitution for the light engine composed of the single MCPCB light engine into the rest of the original luminaire structure that is described with reference to FIGS. 2A-3, hence providing the comparative sample luminaire referred to herein as LUM STD 1.

This luminaire LUM STD 1 was measured by sphere photometry similar to that done with LUM STD 2. The sphere photometry TABLE I lists the spectral parameters for this luminaire under the column marked LUM STD 1. Comparative luminaire sample LUM STD 1 has a nominal 4000K CCT with a color point just slightly below the black body curve as evidenced by the very small negative value for distance to the blackbody locus (Duv). The CRI for LUM STD 1 was 83, which is the mean of the pastel color indices R1 thru R8. The pastel color indices for comparative luminaire sample LUM STD 1 are also listed in TABLE I (depicted in FIG. 5). The CRI value for comparative luminaire sample LUM STD 1 is very close to the 84 CRI value for comparative luminaire sample LUM STD 2.

The saturated color indices R9, R10, R11 and R12 for comparative luminaire sample LUM STD 1 are 13, 71, 84 and 71 for red, yellow, green and blue, respectively. Comparing the saturated color indices for the comparative luminaire sample LUM STD 1 with comparative luminaire sample LUM STD 2, the R9 color indices for LUM STD 1 was measured to be about 3 points lower than for LUM STD 1. The saturated blue index R12 for comparative luminaire sample LUM STD 1 was measured at 71, which was detectably higher and better than LUM STD 2 that has the R12 indices measured at 59. However, R9 was very poor for both the comparative luminaires, i.e., LUM STD 2 and LUM STD 1. The other saturated color indices R10 thru R12 were also very poor for both the comparative luminaires, i.e., LUM STD 2 and LUM STD 1.

The relatively higher value of saturated blue color index R12 for comparative luminaire sample LUM STD 1 may have to do with the broader blue emission in LUM STD 1 as evidenced by the higher FWHM (full width half maximum) for the blue peak in SPD Curve 52 compared to that for Curve 51 for LUM STD 2, as depicted in FIG. 6. The higher FWHM manifests itself in a broader blue peak for curve 52 compared to curve 51. The spectral power distribution (SPD) is graphically depicted in FIG. 6, in which the curve identified by reference number 52 illustrates the spectral power distribution (SPD) captured by the spectrometer attached to the sphere photometry system for the comparative luminaire sample LUM STD 1.

Referring to TABLE I, the color indices measured from the comparative luminaire sample LUM STD 1 for both Caucasian skin tones and Asian skin tones were deficient in a manner similar to the manner in which LUM STD 2 is deficient. Relative to a maximum color index value of 100, the measured R13 index for illumination of Caucasian skin tone was 83 for LUM STD 1, which is low; and the measured R15 index for illumination of Asian skin tone was 76.

Characterization for Test Sample Luminaire Having Enhanced Color Indices for Saturated Colors and Enhanced Color Indices for Caucasion and Asian Skin Tones: QOL A3D LUM Including Multiple Interconnected MCPCB The methods and structures provide herein a light source, such as a luminaire 50, that provides both the light indices for pastels, i.e., indices R1-R8; and high levels for the light indices for saturated light, e.g., R9-R12. In some embodiments, the light source provided herein also provides a light index for Caucasian skin color, i.e., light index R13, and light index for Asian skin color, i.e., light index R15. The luminaires providing these lighting parameters are referred to as luminaire test samples QOL A3D LUM and QOL A5D LUM.

For luminaire test samples QOL A3D LUM, six short length L2 type MCPCB boards of the type shown in FIG. 7 were populated with a 3030 form factor LED. These six MCPCBs were daisy chained, e.g., electrically interconnected by wire connection and solder joint, to form a light engine 75 dimensionally similar to the comparative luminaire sample LUM STD 2, e.g., being a 4' long light engine 75. The light engine 75 provided by the multiple interconnected MCPCBs is inserted as a substitution for the light engine composed of the single MCPCB light engine into the rest of the original luminaire structure that is described with reference to FIGS. 2A-3, hence providing the test sample luminaire referred to herein as QOL A3D LUM.

The lighting characteristics for the test sample luminaire QOL A3D LUM were measured using sphere photometry. TABLE II included in FIG. 8 (hereafter referred to as TABLE II) lists the lighting characteristics and spectral properties that were recorded from QOL A3D LUM, in which the recorded data is listed in the column marked QOL A3D LUM. The CCT of the test sample luminaire QOL A3D LUM was a nominal 4000K, and the chromaticity places the color slightly below the black body curve, as evidenced by the negative distance to the blackbody locus (Duv) of −0.0015. The CRI that was measured from test sample luminaire QOL A3D LUM was 94, which is considered strong performance, and was about 10 points higher than the CRI that was measured from the standard luminaires, i.e., the comparative luminaire sample LUM STD 1 and LUM STD 2. Referring to TABLE II, for QOL A3D LUM each of the pastel color indices R1, R2, R3, R4, R5, R6 and R7 is greater than 90, and the pastel index R8 is 85. The CRI for QOL A3D LUM is the average of the indices R1 through R8 and is 94. The test sample luminaire QOL A3D LUM provides high levels for the light indices for saturated light, e.g., R9-R12. Referring to TABLE II, the saturated color indices R9, R10, R11 and R12 for red, yellow, green and blue, that were measured from the tests sample luminaire QOL A3D LUM were 61, 91, 94 and 75 respectively. Comparison of the saturated color indices measured from test sample luminaire QOL A3D LUM, as recorded in TABLE II, to the saturated color indices measured for the comparative test samples, i.e., LUM STD 1 and LUM STD 2, that were recorded in TABLE I, illustrates that the saturated color indices for the test sample luminaire QOL A3D LUM were considerably higher than the corresponding indices, i.e., saturated indices R9-R12, for the standard luminaires, e.g., LUM STD 1 and LUM STD 2. More specifically, R9 red for example is higher by about 45 points. R10 yellow is higher by at least 15 points. R11 green is higher by at least 10 points. R12 blue is higher by at least 4 points. Thus, red, yellow, green and blue objects would all be rendered more vividly by the test sample luminaire QOL A3D LUM than the same objects being illuminated by the comparative sample luminaires. i.e., LUM STD 1 and LUM STD 2. This will create a more pleasing environment for people who would feel more drawn to the things in the environment. This would in turn lead to a sense of comfort, relaxation and wellness.

Referring to TABLE II, the color indices measured from the test sample luminaire QOL A3D LUM for both Caucasian skin tones and Asian skin tones were enhanced relative to the same color indices measured from the comparative test samples, i.e., LUM STD 1 and LUM STD 2. Relative to a maximum color index value of 100, the measured R13 index for illumination of Caucasian skin tone was 96 for QOL A3D LUM, which is at least 12 points higher relative to the comparative samples LUM STD 1 and LUM STD 2; and the measured R15 index for illumination of Asian skin tone was 92 for QOL A3D LUM, which is at least 15 points higher relative to the comparative samples LUM STD 1 and LUM STD 2. Referring back to TABLE I, the comparative sample luminaires LUM STD 1 and LUM STD 2 had R13 and R15 color indices in the low 80s and mid 70s. This enhanced rendering of the skin tone provided by test sample luminaire QOL A3D LUM is pleasing to people who would feel happy and relaxed in that environment thus promoting a sense of wellness.

Figure 9:
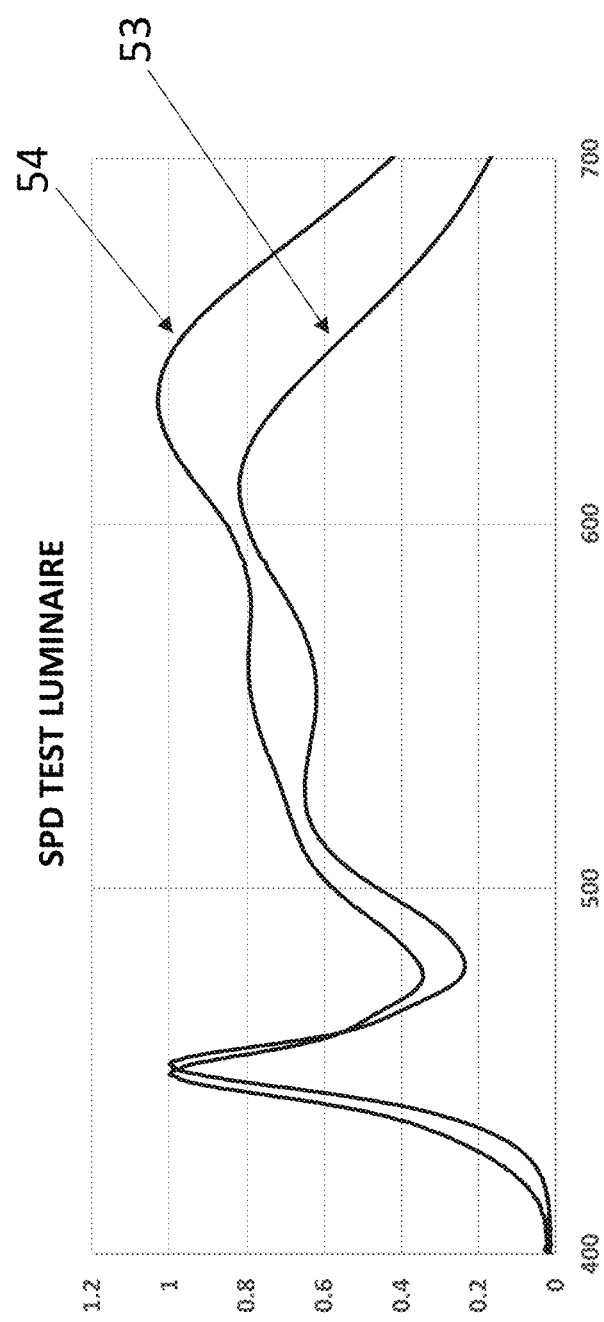
FIG. 9 depicts plots illustrating the spectral power distribution (SPD) of the light emitted by the test luminaire samples, in accordance with some embodiments of the present disclosure.

FIG. 9 shows the normalized SPD of this enhanced luminaire, i.e., test sample luminaire QOL A3D LUM. The normalized SPD is obtained from the regular SPD in the same manner as that described previously. The SPD curve for the test sample luminaire QOL A3D LUM is marked with reference number 53.

Characterization for Test Sample Luminaire Having Enhanced Color Indices for Saturated Colors and Enhanced Color Indices for Caucasion and Asian Skin Tones: QOL A5D LUM Including Multiple Interconnected MCPCB The methods and structures provide herein a light source, such as a luminaire 50, that provides both the light indices for pastels, i.e., indices R1-R8; and high levels for the light indices for saturated light, e.g., R9-R12. In some embodiments, the luminaire provided herein also provides a light index for Caucasian skin color, i.e., light index R13, and light index for Asian skin color, i.e., light index R15. The luminaires providing these lighting parameters are referred to as luminaire test samples QOL A3D LUM and QOL A5D LUM.

For luminaire test samples QOL A5D LUM, six short length L2 type MCPCB boards of the type shown in FIG. 7 were populated with a 2835 form factor LED. These six MCPCBs were daisy chained, e.g., electrically interconnected by wire connection and solder joint, to form a light engine 75 dimensionally similar to the comparative luminaire sample LUM STD 2, e.g., being a 4' long light engine 75. The light engine 75 provided by the multiple interconnected MCPCBs is inserted as a substitution for the light engine composed of the single MCPCB light engine into the rest of the original luminaire structure that is described with reference to FIGS. 2A-3, hence providing the test sample luminaire referred to herein as QOL A5D LUM.

The lighting characteristics for the test sample luminaire QOL A5D LUM were measured using sphere photometry. TABLE II included in FIG. 8 (hereafter referred to as TABLE II) lists the lighting characteristics and spectral properties that were recorded from QOL A5D LUM, in which the recorded data is listed in the column marked QOL A5D LUM.

The CCT measured from test sample QOL A5D LUM was 3819 which falls within the ANSI 4000K tolerance. While 4000K nominal CCT is shown in TABLE II, the CCT of these luminaires, i.e., test sample luminaires QOL A5D LUM and QOL A3D LUM can be anything from 3500K to 5000K.

The lumens per watt (LPW) of luminaires QOL A3D LUM and QOL A5D LUM can be between 95 and 125. The chromaticity places the color below the black body curve as evidenced by the distance to the blackbody locus (Duv) of −0.0042. The CRI measured from QOL A5D LUM was good at 96, which is about 12 points higher than the CRI in the comparative samples LUM STD 1 and LUM STD 2

Each of the eight pastel color indices R1 thru R8 is >90 including pastel index R8 was present in the light emitted by test sample. The CRI of 96 is the average of the indices R1 through R8. Pastel colors emitted by QOL A5D LUM are likely to be very pleasing to humans under this luminaire, i.e., test sample luminaire QOL A5D LUM.

The test sample luminaire QOL A5D LUM provides high levels for the light indices for saturated light, e.g., R9-R12. Referring to TABLE II, the saturated color indices R9, R10, R11 and R12 for red, yellow, green and blue, that were measured from the tests sample luminaire QOL A5D LUM were 92, 96, 93 and 86 respectively. Therefore, for test sample luminaire QOL A5D LUM, the light emitted for the saturated light indices are all substantially greater than 85.

Comparison of the saturated color indices measured from test sample luminaire QOL A5D LUM, as recorded in TABLE II, to the saturated color indices measured the comparative test samples, i.e., LUM STD 1 and LUM STD 2, that were recorded in TABLE I, illustrates that the saturated color indices for the test sample luminaire QOL A5D LUM were considerably higher than the corresponding indices, i.e., saturated indices R9-R12, for the standard luminaires, e.g., LUM STD 1 and LUM STD 2. For the standard luminaires, the R9 index was measured to be between 13 and 16, the R10 index was measured to be between 71 and 76, the R11 was measured to be between 80 and 84 and the R12 index was measured to be between 59 and 71. Not only are these values measured from QOL A5D all considerably higher than the corresponding indices for the standard luminaires, Lum Std 1 and Lum Std 2, but these saturated color indices are also higher than the corresponding indices for the enhanced luminaire QOL A3D LUM. To reiterate, for the test sample luminaire QOL A5D LUM saturated color indices R9, R10, R11 and R12 for red, yellow, green and blue for test are 92, 96, 93 and 86, respectively.

Thus, saturated color red, yellow, green and blue objects would all be rendered very vividly by test sample luminaire QOL A5D LUM. This creates a pleasing environment for the human who would feel more drawn to the things in the environment leading to a sense of comfort, relaxation and wellness.

Turning to skin tones, the indices R13 and R15 for test sample luminaire QOL A5D LUM were measured to be 98 and 96, respectively. These values for the indices R13 and R15 of test sample luminaire QOL A5D LUM were significantly higher than the low 80s and mid 70s values for the indices R13 and R15 that was measured for the comparative sample luminaires, LUM STD 1 and LUM STD 2, and higher than those for the enhanced luminaire QOL A3D LUM. It is believed that this enhanced rendering of the skin tone is pleasing to humans who feel happy and relaxed in that environment thus promoting a sense of wellness.

FIG. 9 shows the normalized SPD of this enhanced luminaire. The normalized SPD is obtained from the regular SPD in the same manner as that described previously. The SPD curve for the test sample luminaire QOL A5D LUM is marked with reference number 54.

It is observed from FIG. 9 that the SPD for QOL A5D LUM differs from QOL A3D LUM in several ways. Starting from about 480 nm, the normalized SPD curve for QOL A5D LUM lies above that of QOL A3D LUM thru the rest of the visible spectrum. In other words, the normalized intensity of the QOL A5D LUM luminaire SPD exceeds that of the QOL A3D LUM luminaire from the end of the blue region (around 480 nm) through the end of the visible spectrum (700 nm). Also, the magnitude of the difference between the normalized SPDs of the two luminaires QOL A3D LUM and QOL A5D LUM is higher in the red region of the spectrum for wavelengths >=610 nm. In addition, while the SPD of the luminaire QOL A3D LUM displays a distinct local valley between 520 nm and 600 nm, the SPD for the luminaire QOL A5D LUM does not show this valley.

Summation of Spectral Parameters for Luminaires

In TABLE III depicted in FIG. 10, the spectral properties of the comparative sample luminaires, LUM STD 1 and LUM STD 2 and the test sample luminaires, i.e., enhanced luminaires QOL A3D LUM and QOL A5D LUM, may be compared.

There was a clear increase in the CRI metric for the enhanced luminaires, i.e., QOL A3D LUM and QOL A5D LUM, relative to the standard luminaires, i.e., LUM STD 1 and LUM STD 2. The CRI metric for the enhanced luminaires, e.g., QOL A3D LUM and QOL A5D LUM was equal to 94 or greater, whereas the CRI metric for the comparative sample luminaires, i.e., LUM STD 1 and LUM STD 2, was equal to 84 or less.

Turning to the pastel color indices of light emitted by the luminaires, for pastel color index R1, the enhanced luminaires, i.e., QOL A3D LUM and QOL A5D LUM, recorded values of greater than 96, while the comparative sample luminaires, i.e., LUM STD 1 and LUM STD 2, recorded values that were equal to 82. For pastel color index R2, the enhanced luminaires, i.e., QOL A3D LUM and QOL A5D LUM, recorded values greater than 96, and the comparative sample luminaires, i.e., LUM STD 1 and LUM STD 2, recorded values that were equal to 90 or less. Turning to the pastel color index R3, the enhanced luminaires, i.e., QOL A3D LUM and QOL A5D LUM, and the comparative sample luminaires, i.e., LUM STD 1 and LUM STD 2, have very similar measured values ranging from 92-96. The performance of the pastel color index of R4 also indicated increased performance for the enhanced luminaires, i.e., QOL A3D LUM and QOL A5D LUM, in which the R4 index was measured to be equal 94 or greater. By comparison the R4 index for the comparative sample luminaires, i.e., LUM STD 1 and LUM STD 2, was equal to 84 or less. In one example, pastel color index R5 was measured from the enhanced luminaires, i.e., QOL A3D LUM and QOL A5D LUM, to be equal to 95 or greater, while compared to comparative sample luminaires, i.e., LUM STD 1 and LUM STD 2, which were equal to 83 or less. Referring now to the pastel color index R6, the measured performance for enhanced luminaires, i.e., QOL A3D LUM and QOL A5D LUM, was equal to 94 or greater, whereas the measured R6 performance for standard luminaires, i.e., LUM STD 1 and LUM STD 2, may be equal to 86 or less.

Pastel color index R7 for the enhanced luminaires, i.e., QOL A3D LUM and QOL A5D LUM, was equal to 94 or greater, whereas the pastel color index R7 for standard luminaires, i.e., LUM STD 1 and LUM STD 2, may be equal to 87 or less. Pastel color index R8 with the enhanced luminaires, i.e., QOL A3D LUM and QOL A5D LUM, was equal to 85 or greater, while pastel color index R8 for standard luminaires, i.e., LUM STD 1 and LUM STD 2, may be equal to 68 or less.

Turning to the saturated color indices, i.e., R9, R10, R11, and R12, for light emitted by the luminaires, even higher advances in performance was measured in these regions of light emission for the enhanced luminaires, i.e., QOL A3D LUM and QOL A5D LUM, when compared to the comparative luminaires (standard luminaires), i.e., LUM STD 1 and LUM STD 2. For example, for the saturated color index R9 corresponding to red light, the enhanced luminaires, i.e., QOL A3D LUM and QOL A5D LUM, were recorded at having an R9 index being equal to 61 or greater. In comparison, for the saturated color index R9 corresponding to red light, the standard luminaires, i.e., comparative samples (LUM STD 1 and LUM STD 2), were recorded at having an R9 index being equal to 16 or less. Turning to the saturated color index R10 corresponding to yellow light, the enhanced luminaires, i.e., QOL A3D LUM and QOL A5D LUM, had an R10 value equal to 91 or greater, while standard luminaires, i.e., the comparative samples LUM STD 1 and LUM STD 2, had an R10 value equal to 76 or less. The saturated color index R11 corresponds to green light. The enhanced luminaires, i.e., QOL A3D LUM and QOL A5D LUM, had an R11 value equal to 93 or greater, while standard luminaires, i.e., the comparative samples LUM STD 1 and LUM STD 2, had an R11 value equal to 84 or less. Turning to the saturated color index R12 correlated to blue light, the enhanced luminaires, i.e., QOL A3D LUM and QOL A5D LUM, had an R12 value equal to 75 or greater, while standard luminaires, i.e., the comparative samples LUM STD 1 and LUM STD 2, had an R12 value equal to 71 or less.

As discussed previously, it is advantageous to design luminaires/fixtures that produce a spectrum with a high quality of light that renders skin tones well resulting in a calm, comfortable and relaxed environment that in turn promotes human wellness. R13 is relevant for Caucasian skin tone, while R15 is relevant for Asian skin tone.

Referring first to the skin tone index R13 for Caucasian skin tone, the enhanced luminaires, i.e., QOL A3D LUM and QOL A5D LUM, the R13 index was equal to 96 or greater on a scale to 100, while for the standard luminaires, i.e., comparative sample luminaires LUM STD 1 and LUM STD 2, the measured R13 index was 84 or less.

Turning to the skin tone index R15 for Asian skin tone, the enhanced luminaires, i.e., QOL A3D LUM and QOL A5D LUM, the R15 index was equal to 92 or greater on a scale to 100, while for the standard luminaires, i.e., comparative sample luminaires LUM STD 1 and LUM STD 2, the measured R15 index was 77 or less.

The TM-30 Fidelity Metric Rf for the enhanced luminaires, i.e., QOL A3D LUM and QOL A5D LUM, is greater than 90 compared to 82 for standard luminaire, i.e., comparative sample luminaires LUM STD 1 and LUM STD 2.

The TM-30 Gamut Metric Rg for the enhanced luminaires, i.e., QOL A3D LUM and QOL A5D LUM, is greater than 101 compared to 98 or less for a standard luminaire, i.e., comparative sample luminaires LUM STD 1 and LUM STD 2.

Thus, pastel color rendition, saturated color rendition and skin tone rendition are all much superior for the enhanced luminaires, i.e., QOL A3D LUM and QOL A5D LUM, which have special spectral power distributions (SPDs). The shape and relative intensity of the spectral power distributions (SPDs) for QOL A3D LUM and QOL A5D LUM lead to the high value of the color rendition indices. This creates a more pleasing environment for people who would feel more drawn to the objects leading to a sense of comfort, relaxation and wellness. This also leads to enhanced rendering of the skin tone which is pleasing to humans who feel happy and relaxed in that environment thus promoting a sense of wellness.

Comparison of Spectral Power Distributions (SPD) of Test Sample Luminaire (Enhanced Luminaire) to Comparative Sample Luminaire.

FIG. 11 is an overlay of the normalized spectral power distributions of the two standard luminaires LUM STD 1 and LUM STD 2 and the two enhanced luminaires QOL A3D LUM and QOL A5D LUM. The spectral parameters discussed previously for these four luminaires result directly from the shape and local intensity of these SPD curves. In addition, the differences in the spectral parameters between the luminaires are due to differences in the individual SPD curves. It is the differences in the SPD curves that result in some luminaires creating a sense of wellness vs others.

Referring to FIG. 11, the SPD curve for the comparative sample luminaire LUM STD 1 is marked with reference number 52; the SPD curve for the comparative sample luminaire LUM STD 2 is marked with reference number 51; the SPD curve for the test sample luminaire QOL A3D LUM is marked with reference number 53; and the SPD curve for the test sample luminaire QOL A5D LUM is marked with reference number 54.

Deep analysis of these SPD curves provides an understanding of the differences in the spectral energy emission over the entire visible spectrum from 400 nm to 700 nm, between the various luminaires. One needs to understand if the enhanced luminaires QOL A3D LUM and QOL A5D LUM are preferentially emitting more energy in certain wavelength regions compared to other wavelength regions and how this differs between the standard luminaires and the enhanced luminaires.

To do this the area under each SPD curve is computed. From a mathematical view point, the area under a curve between any two x co-ordinates is the integral of ydx between these two x co-ordinates and is denoted by ∫ydx. The wavelength domain between 400 nm and 700 nm is divided into 20 nm wide intervals.

The SPD data from the sphere photometry spectrometer is available in 0.25 nm wide intervals and the area of each of these 0.25 nm wide rectangles under the SPD curve is calculated and then added up between specified wavelength end points for each 20 nm wide region: 400 nm-420 nm, 420 nm-440 nm etc. going all the way to 680 nm-700 nm. Each of these regional areas is then divided by the total area under the pertinent SPD curve to get the % area per 20 nm wide region. This is shown in TABLE IV that is included in FIG. 12. The sum of all the % area values in each of the four columns of data in TABLE IV is 100%.

Analysis of Area Under the Spectral Power Distributions (SPD) Curves for the Luminaires The area for under the SPD distribution curves for each of the luminaires, i.e., LUM STD 1, LUM STD 2, QOL A3D LUM and QOL A5D LUM, is recorded in TABLE IV, which is included in FIG. 12. The primary SPD difference between the standard luminaires, i.e., comparative samples LUM STD 1 and LUM STD 2, and the enhanced luminaires that promotes wellness, i.e., test samples QOL A3D LUM and QOL A5D LUM, starts from green wavelengths greater than about 540 nm. More specifically, in some embodiments, when comparing the area below the SPD curves for wavelengths ranging from 540 nm to 560 nm, which is within the green region of light emission, the enhanced luminaires emit less spectral energy in comparison to the standard luminaires. For example, the measured area of the SPD curve within the 540 nm to 560 nm portion of light emission for the enhanced luminaires, i.e., QOL A3D LUM and QOL A5D LUM, was 7.85%-8.24% which is a lesser area when compared to the area beneath the same range of light wavelengths for the standard luminaires, i.e., LUM STD 1 and LUM STD 2, which was equal to 9.2%-9.38%. The enhanced luminaires, i.e., QOL A3D LUM and QOL A5D LUM, also emit less spectral energy in the 560-580 nm yellow region compared to the standard luminaires, i.e., LUM STD 1 and LUM STD 2. For example, the area underlying the curve for the SPD of the enhanced luminaires in the 560 nm to 580 nm was 7.94%-8.68%, which was a lesser value when compared to 10.29%-10.54% value for the area underlying the SPD curve of the standard luminaires, i.e., LUM STD 1 and LUM STD 2, for the same wavelengths, i.e., 560 nm to 580 nm. Again, the enhanced luminaires, i.e., QOL A3D LUM and QOL A5D LUM, emit less spectral energy in the 580-600 nm orange-amber region compared to the standard luminaires, LUM STD 1 and LUM STD 2. For example, the portion for the spectral energy emitted by the enhanced luminaires in the wavelengths ranging from 580 nm to 600 nm may range from 8.18%-10% compared to 11.08%-11.35% for the spectral energy emitted by the standard luminaires in the wavelengths ranging from 580 nm to 600 nm.

In summation for wavelengths that are less than approximately 600 nm, the enhanced luminaires that promote human wellness, e.g., the enhanced luminaires, i.e., QOL A3D LUM and QOL A5D LUM, emit less spectral energy in the 540-600 nm region than standard luminaires, e.g., LUM STD 1 and LUM STD 2.

In the 600 nm to the 620 nm region of the SPD curves for the enhanced luminaires, i.e., QOL A3D LUM and QOL A5D LUM, and standard luminaires, e.g., LUM STD 1 and LUM STD 2, there was no clear difference between the spectral energy emitted by the enhanced luminaire and the standard luminaire. For example, in this instance, the % areas overlap, in which 9.28%-10.73% is the portion of area beneath the SPD curve for the enhanced luminaires versus 10.56%-10.89% for the portion of area beneath the SPD curve for the standard luminaires.

A clear difference between the enhanced luminaires, i.e., QOL A3D LUM and QOL A5D LUM, that promote human wellness and the standard luminaires, e.g., LUM STD 1 and LUM STD 2, was measurable for the wavelengths of emitted light in the red and deep red. In one embodiment, the enhanced luminaires emit more spectral energy in the 620 nm to 640 nm red region compared to the standard luminaires. The percentage of area beneath the SPD curve for the enhanced luminaires, i.e., QOL A3D LUM and QOL A5D LUM, range from 9.68%-10.23%, which illustrates the increased spectral energy provided by the enhanced luminaires, i.e., QOL A3D LUM and QOL A5D LUM, when compared to the standard luminaires, i.e., comparative sample luminaires LUM STD 1 and LUM STD 2, which had values ranging from 8.56%-8.95%.

Turning to deeper reds, the data recorded in TABLE IV illustrated that the enhanced luminaires, i.e., QOL A3D LUM and QOL A5D LUM, emit more spectral energy in the 640-660 nm deep red region compared to the standard luminaires, i.e., comparative sample luminaires LUM STD 1 and LUM STD 2. For example, the percentage of area beneath the SPD curve for the enhanced luminaires, i.e., QOL A3D LUM and QOL A5D LUM, range from 7.36%-9.69%, which illustrates the increased spectral energy provided by the enhanced luminaires, i.e., QOL A3D LUM and QOL A5D LUM, when compared to the standard luminaires, i.e., comparative sample luminaires LUM STD 1 and LUM STD 2, which had values ranging from 5.97%-6.38%.

The enhanced luminaires, i.e., QOL A3D LUM and QOL A5D LUM, emit more spectral energy in the 660 nm to 680 nm deeper red region compared to the standard luminaires. In this example, the 4.9%-7.73% value for the area underlying the SPD curve of the enhance luminaires within the wavelength region ranging from 660 nm to 680 nm was greater than the 3.7%-4.07% value for the area underlying the SPD curve of the standard luminaires within the wavelength region ranging from 660 nm to 680 nm.

A clear difference is further observed between the enhanced luminaires, i.e., QOL A3D LUM and QOL A5D LUM, that promote human wellness and the standard luminaires, e.g., LUM STD 1 and LUM STD 2, for the wavelengths of emitted light being characterized in the red and deeper red. In one embodiment, the enhanced luminaires emit more spectral energy in the 680 nm to 700 nm deeper red region compared to the standard luminaires. The percentage of area beneath the SPD curve for the enhanced luminaires, i.e., QOL A3D LUM and QOL A5D LUM, range from 2.98%-5.35%, which illustrates the increased spectral energy provided by the enhanced luminaires, i.e., QOL A3D LUM and QOL A5D LUM, when compared to the standard luminaires, i.e., comparative sample luminaires LUM STD 1 and LUM STD 2, which had values ranging from 2.15%-2.39%.

The enhanced luminaire that can promote human wellness via the spectrum of light that it emits will have a normalized SPD with the attributes shown in the last two columns of TABLE IV that is depicted in FIG. 12, which correspond to the lighting characteristics measured from the enhanced luminaires, i.e., QOL A3D LUM and QOL A5D LUM. The last two columns of TABLE IV are reproduced herein as TABLE V, as follows:

TABLE V

| Nm | QOL A3D LUM % Area | QOL A5D LUM % Area |
| --- | --- | --- |
| 400-420 | 0.36 | 0.51 |
| 420-440 | 1.98 | 2.69 |
| 440-460 | 10.08 | 8.03 |
| 460-480 | 4.58 | 4.15 |
| 480-500 | 4.34 | 4.65 |
| 500-520 | 7.59 | 6.47 |
| 520-540 | 8.52 | 7.24 |
| 540-560 | 8.24 | 7.85 |
| 560-580 | 8.68 | 7.94 |
| 580-600 | 10 | 8.18 |
| 600-620 | 10.73 | 9.28 |
| 620-640 | 9.68 | 10.23 |
| 640-660 | 7.36 | 9.69 |
| 660-680 | 4.9 | 7.73 |
| 680-700 | 2.98 | 5.35 |

TABLE V illustrates the bounds of % area under the normalized SPD curve as a function of wavelength for an enhanced luminaire that can promote human wellness. This SPD area criteria can be used to determine the shape and intensity of the SPD curve such that the spectral parameters mentioned before, like the R1 thru R15 indices and TM-30 Rf and Rg, are suitably high for human sense of wellness.

It follows from TABLE V, for example, that the area under the normalized SPD curve between 540-560 nm, for an enhanced luminaire promoting human wellness, should be between 7.8% and 8.25%. Again, as another example, in the wavelength region between 620 nm and 640 nm, the area under the normalized SPD curve can be between 9.7% and 10.2% for an enhanced luminaire promoting human wellness. Each of the wavelength regions in TABLE V can be used to formulate an embodiment for the % area for this enhanced luminaire.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Spatially relative terms, such as "forward", "back", "left", "right", "clockwise", "counter clockwise", "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Having described preferred embodiments of a luminaire for enhanced color rendition and wellness, it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method of lighting that promotes human wellness by increasing representation of saturated color indices in lighting, the method including:

employing a luminaire with a normalized spectral power distribution (SPD) curve for promoting human wellness, the normalized SPD curve having the following percentage areas for the following wavelength domains, the normalized SPD curve comprising spectral energy in a 620 nm to 640 nm region of the SPD curve ranging from 9.5% to 10.5% of a total of an area for a normalized SPD curve, spectral energy in a 640 nm to 660 nm region of the SPD curve ranging from 7.25% to 9.8% of the total of the area of the normalized SPD curve, spectral energy in a 660 nm to 680 nm region of the SPD curve ranging from 4.8% to 7.8% of the total of the area for the normalized SPD curve, and spectral energy in a 680 nm to 700 nm region of the SPD curve ranging from 2.75% to 5.5% of the total of the area for the normalized SPD curve; and illuminating an area with the luminaire to provide color indices for saturated light selected from the group consisting of R9, R10, R11, R12 and combinations thereof, the color indices for saturated light having a values of greater than 60.

2. The method of claim 1, wherein an initial portion of the remainder of the spectral energy comprises:

spectral energy in a 540 nm to 560 nm region of the SPD curve ranging from 7.85% to 8.25% of the total for the area of the normalized SPD curve;

spectral energy in a 560 nm to 580 nm region of the SPD curve ranging from 7.95% to 8.7% of the total for the area of the normalized SPD curve; and spectral energy in a 580 nm to 600 nm region of the SPD curve ranging from 8.15% to 10% of the total for the area of the normalized SPD curve; and spectral energy in the 600 nm to 620 nm region of the SPD curve ranging from 9.15% to 10.75% of the total for the area of the normalized SPD curve.

3. The method of claim 1, wherein the saturated light has saturated color indices selected from the group consisting of R9 ranging from 60 to 95, R10 ranging from 91 to 96, R11 ranging from 90 to 95, R12 ranging from 75 to 86, and combinations thereof.

4. The method of claim 1, wherein the color correlated temperature ranges from 3500K to 5000K.

5. The method of claim 1, wherein the lumens per watt (LPW) ranges from 95 to 125.

6. The luminaire of claim 1, wherein the solid state light emitters comprise light emitting diodes (LEDs).

7. The luminaire of claim 1, wherein the light emitting diodes (LEDs) are surface mount devices having a 3030 or 2835 form factor.

8. A method of lighting comprising:

employing a luminaire with a normalized spectral power distribution (SPD) curve for promoting human wellness, the normalized SPD curve having the following percentage areas for the following wavelength domains, the normalized SPD curve comprising spectral energy in a 620 nm to 640 nm region of the SPD curve ranging from 9.5% to 10.5% of a total of an area for a normalized SPD curve, spectral energy in a 640 nm to 660 nm region of the SPD curve ranging from 7.25% to 9.8% of the total of the area of the normalized SPD curve, spectral energy in a 660 nm to 680 nm region of the SPD curve ranging from 4.8% to 7.8% of the total of the area for the normalized SPD curve, and spectral energy in a 680 nm to 700 nm region of the SPD curve ranging from 2.75% to 5.5% of the total of the area for the normalized SPD curve; and illuminating an area with the luminaire to provide color indices for illuminating skin tones is R13, the color indices of R13 for illuminating skin tones having values of greater than 90.

9. The method of claim 8, wherein the color indices for illuminating skin tones is R13 being equal to 95 or greater, and is used for illuminating Caucasian skin tone.

10. The method of claim 8, wherein an initial portion of the remainder of the spectral energy comprises:

spectral energy in a 540 nm to 560 nm region of the SPD curve ranging from 7.85% to 8.25% of the total for the area of the normalized SPD curve;

spectral energy in a 560 nm to 580 nm region of the SPD curve ranging from 7.95% to 8.7% of the total for the area of the normalized SPD curve;

spectral energy in a 580 nm to 600 nm region of the SPD curve ranging from 8.15% to 10% of the total for the area of the normalized SPD curve; and spectral energy in the 600 nm to 620 nm region of the SPD curve ranging from 9.15% to 10.75% of the total for the area of the normalized SPD curve.

11. The method of claim 8, wherein the color correlated temperature ranges from 3500K to 5000K.

12. The method of claim 8, wherein the lumens per watt (LPW) ranges from 95 to 125.

13. The luminaire of claim 8, wherein the solid state light emitters comprise light emitting diodes (LEDs).

14. The luminaire of claim 8, wherein the light emitting diodes (LEDs) are surface mount devices having a 3030 or 2835 form factor.

15. A method of lighting comprising:

employing a luminaire with a normalized spectral power distribution (SPD) curve for promoting human wellness, the normalized SPD curve having the following percentage areas for the following wavelength domains, the normalized SPD curve comprising spectral energy in a 620 nm to 640 nm region of the SPD curve ranging from 9.5% to 10.5% of a total of an area for a normalized SPD curve, spectral energy in a 640 nm to 660 nm region of the SPD curve ranging from 7.25% to 9.8% of the total of the area of the normalized SPD curve, spectral energy in a 660 nm to 680 nm region of the SPD curve ranging from 4.8% to 7.8% of the total of the area for the normalized SPD curve, and spectral energy in a 680 nm to 700 nm region of the SPD curve ranging from 2.75% to 5.5% of the total of the area for the normalized SPD curve; and illuminating an area with the luminaire to provide color indices for illuminating skin tones is R15, the color indices of R15 for illuminating skin tones having values of greater than 90.

16. The method of claim 15, wherein the color indices for illuminating skin tones is R15 being equal to 92 or greater, and is used for illuminating Asian skin tone.

17. The method of claim 15, wherein an initial portion of the remainder of the spectral energy comprises:
- spectral energy in a 540 nm to 560 nm region of the SPD curve ranging from 7.85% to 8.25% of the total for the area of the normalized SPD curve;
- spectral energy in a 560 nm to 580 nm region of the SPD curve ranging from 7.95% to 8.7% of the total for the area of the normalized SPD curve;
- spectral energy in a 580 nm to 600 nm region of the SPD curve ranging from 8.15% to 10% of the total for the area of the normalized SPD curve; and
- spectral energy in the 600 nm to 620 nm region of the SPD curve ranging from 9.15% to 10.75% of the total for the area of the normalized SPD curve.

18. The method of claim 15, wherein the color correlated temperature ranges from 3500K to 5000K.

19. The method of claim 15, wherein the lumens per watt (LPW) ranges from 95 to 125.

20. The luminaire of claim 15, wherein the solid state light emitters comprise light emitting diodes (LEDs).